United States Patent
Kellner et al.

(10) Patent No.: US 8,951,472 B2
(45) Date of Patent: *Feb. 10, 2015

(54) PORTABLE FLUORIMETRIC APPARATUS, METHOD AND SYSTEM

(75) Inventors: David G. Kellner, Urbana, IL (US); Debapriya Mazumdar, Chicago, IL (US)

(73) Assignee: ANDalyze, Inc., Champaign, IL (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/838,740

(22) Filed: Jul. 19, 2010

(65) Prior Publication Data

US 2012/0015445 A1    Jan. 19, 2012

(51) Int. Cl.
*G01N 15/06* (2006.01)
*G01N 21/64* (2006.01)

(52) U.S. Cl.
CPC .......... *G01N 21/645* (2013.01); *G01N 21/6428* (2013.01); *G01N 2201/0221* (2013.01)
USPC ......... 422/68.1; 422/69; 422/82.08; 436/169; 436/501; 436/172

(58) Field of Classification Search
None
See application file for complete search history.

(56) References Cited

U.S. PATENT DOCUMENTS

| | | | |
|---|---|---|---|
| 4,126,418 A * | 11/1978 | Krasnow | 422/64 |
| 4,312,459 A * | 1/1982 | Leach | 220/256.1 |
| 4,434,235 A | 2/1984 | Rabi et al. | |
| 5,830,344 A | 11/1998 | Priddy et al. | |
| 6,999,173 B2 | 2/2006 | Kleinfeld et al. | |
| 7,192,708 B2 * | 3/2007 | Lu et al. | 435/6.12 |
| 7,459,713 B2 | 12/2008 | Coates | |
| 7,660,678 B2 | 2/2010 | Odegard et al. | |
| 2004/0161778 A1 | 8/2004 | Lu et al. | |
| 2005/0282186 A1 | 12/2005 | Lu et al. | |
| 2006/0146315 A1 | 7/2006 | Treado | |
| 2007/0189923 A1 | 8/2007 | Lenhard et al. | |
| 2008/0192249 A1 | 8/2008 | Babichenko et al. | |
| 2009/0004753 A1 | 1/2009 | Antoulinakis et al. | |
| 2009/0125271 A1 | 5/2009 | Mizumoto et al. | |
| 2009/0181451 A1 | 7/2009 | Slowey et al. | |

(Continued)

OTHER PUBLICATIONS

Carlson, M. A., et al. An automated, handheld biosensor for aflatoxin, 2000, Biosensors & Bioelectronics, vol. 14, pp. 841-848.*

(Continued)

*Primary Examiner* — Robert Xu
(74) *Attorney, Agent, or Firm* — Nancy R. Gamburd; Gamburd Law Group LLC

(57) ABSTRACT

A fluorimetric system, apparatus and method are disclosed to measure an analyte concentration in a sample. A sensor reagent housing is also disclosed which comprises a channel and a porous medium having an analysis chemistry reagent, such as a nucleic acid analysis chemistry reagent. The apparatus and system are portable for field use, with an apparatus housing having a size adapted to fit into a user's hand. An apparatus also includes a sensing chamber and cover, a user interface, a light source, a photomultiplier tube, an amplifier, an A/D converter, a memory, and a processor. In various embodiments, the processor performs a data fitting, determines a sample reaction rate parameter, and determines the analyte concentration from a comparison of the sample reaction rate parameter with stored calibration data. The processor may also generate the calibration data and site-specific offset factors, and modify the calibration data using an offset factor.

66 Claims, 15 Drawing Sheets

(56) References Cited

U.S. PATENT DOCUMENTS

2010/0151579 A1 6/2010 Wang et al.
2011/0008909 A1 1/2011 Homrig et al.

OTHER PUBLICATIONS

Stevens, D. Y. et al., On-card dry reagent storage for disposable microfluidic immunoassays, 2008, 12th International Conference on Miniaturized Systems for Chemistry and Life Sciences, Oct. 12-16, 2008, San Diego, California, USA, pp. 188-190.*
Savitzky, A., et al., Smoothing and Differentiation of data by simplified least squares procedures, 1964, Analytical Chemistry, vol. 36(8), pp. 1627-1639.*
Field Sampling Procedures Manual, Chapter 7 Field Analysis, 2006, pp. 1-19. retrieved from internet: http://web.archive.org/web/20061011020242/http://www.nj.gov/dep/srp/guidance/fspm/pdf/chapter07.pdf.*

* cited by examiner

FIG. 17

Calibration

Lead

Performing the calibration requires 3 standardized solutions from ANDalyze:

25, 50, 75 ppb

Press Next to get started.

[Next]  [Cancel]

FIG. 18

Select Site

*None*
*New Site*

Factor: n/a
Press ◁▷ to change action.

◁ [Select] ▷  [Cancel]

FIG. 19

New Site
Enter up to 8 characters.

CHM DI

```
1 2 3 ⊂ A B C D E F G
4 5 6 ← H I J K L M N
7 8 9 ⇧ O P Q R S T U
0 - .   [ ] V W X Y Z
```

[Save]  [Cancel]

FIG. 20

Site Calibration

Lead

Site: CHM DI
Step 1 of 2:
Please insert sample water spiked with Lead.

[Start]  [Cancel]

FIG. 21

Site Calibration

Lead

Site: CHM DI
Step 2 of 2:
Please insert plain sample-water.

[Start]  [Cancel]

FIG. 22

Calibration Results

Lead

Site: CHM DI
Factor: 0.174369
Sample-water conc:

*BELOW LIMIT*

[Apply]  [Cancel]

PORTABLE FLUORIMETRIC APPARATUS, METHOD AND SYSTEM

CROSS-REFERENCE TO A RELATED APPLICATION

This application is related to and claims priority to U.S. patent application Ser. No. 12/838,762, filed concurrently herewith, inventors Debapriya Mazumdar et al., entitled "Sensor Housing and Reagent Chemistry" (the "related application"), which is commonly assigned herewith, the entire contents of which are incorporated herein by reference with the same full force and effect as if set forth in their entirety herein, and with priority claimed for all commonly disclosed subject matter.

FIELD OF THE INVENTION

The present invention in general is related to fluorimeter technology and, in particular, is related to an apparatus, method and system for detection of heavy metal ion concentrations using nucleic acid-based fluorimetry.

BACKGROUND OF THE INVENTION

Methods which permit real time detection of lead ions ($Pb^{2+}$) and other metal ions are very important in the fields of environmental monitoring, clinical toxicology, wastewater treatment, and industrial process monitoring and can lead to preventative measures or lower risks associated with metal contaminants. Traditional methods of detecting metal ions are cumbersome, however, often requiring samples collected in the field to be brought back and analyzed in a laboratory setting. Methods are needed for real time detection and monitoring of metal ions in industrial and biological systems.

Fluorescence spectroscopy is a technique well suited for detection of very small concentrations of analytes. Fluorescence provides significant signal amplification, since a single fluorophore can absorb and emit many photons, leading to strong signals even at very low concentrations. In addition, the fluorescence time-scale is fast enough to allow real-time monitoring of concentration fluctuations. Fluorescent properties only respond to changes related to the fluorophore, and therefore can be highly selective.

Commercially available fluorimeters, designed to measure fluorescence signals, however, are typically bulky, heavy, require an AC input voltage or current for power, and are ill-suited for use in the field. Such fluorimeters typically require significant sample preparation, and often as many as twelve or more steps to obtain an analytic result, which generally must be carried out in a laboratory setting. In addition, many if not all commercially available fluorimeters are incapable of measuring extremely small concentrations of analytes such as lead, in the parts per billion ("ppb") range. In many instances, new environmental laws and regulations requiring testing to the level of ppb, such as newer regulations being promulgated by the U.S. Environmental Protection Agency ("EPA"). Accordingly, a need remains for a portable fluorimeter apparatus and system which is highly sensitive, capable of detecting analytes in the parts per billion range, and which is suited for field use.

SUMMARY

Exemplary embodiments of the invention provide an apparatus, method and system for highly-sensitive detection of heavy metal ion concentrations using exemplary nucleic acid-based fluorimetry, such as for the detection of concentrations of ions such as lead, uranium, copper, mercury, cadmium, silver, etc., in drinking water and in various environmental water sources, such as rivers, lakes, aquifers, wells, for example. Concentrations of such ions may be detected as low as a parts per billion (ppb) level, using just several user-friendly steps. The exemplary embodiments provide a general platform for sensing any type of fluorescence for detection of any corresponding substance, in addition to the exemplary detection of heavy metal ions using such exemplary nucleic acid-based reagents.

In an exemplary embodiment, a fluorimetric system to determine an analyte concentration in a sample is disclosed, with the exemplary system comprising: a sensor reagent housing; and a fluorimetric apparatus. An exemplary fluorimetric apparatus comprises: an apparatus housing; a sensing chamber within the apparatus housing, the sensing chamber to hold a cuvette; a sensing chamber cover movably coupled to the apparatus housing, the sensing chamber cover and apparatus housing together forming an inner light baffle and an outer light baffle over and around an upper portion of the sensing chamber; a user interface arranged on an exterior of the apparatus housing; a light source within an interior of the apparatus housing in optical communication with the sensing chamber to provide light to the sensing chamber; a photomultiplier tube within the interior of the apparatus housing in optical communication with the sensing chamber to receive a fluorescence signal from the sensing chamber and generate a corresponding fluorescence voltage signal; an amplifier within the interior of the apparatus housing and coupled to the photomultiplier tube to amplify the fluorescence voltage signal; an analog-to-digital converter within the interior of the apparatus housing and coupled to the amplifier to generate a plurality of digital fluorescence sample data values in response to the amplified fluorescence voltage signal; a memory within the interior of the apparatus housing, the memory to store calibration data; and a processor within the interior of the apparatus housing and coupled to the memory and to the analog-to-digital converter to receive the digital fluorescence sample data values and to determine an analyte concentration of the sample.

In an exemplary embodiment, the sensor reagent housing comprises: a channel; and a porous medium in the channel, the porous medium having an analysis chemistry reagent. Also in an exemplary embodiment, the analysis chemistry reagent is a nucleic acid analysis chemistry reagent. The sensor reagent housing may further comprise a nozzle fitting couplable to a syringe for injection of the sample through the channel and porous medium for collection in the cuvette.

In various exemplary embodiments, the processor further is to perform a data fitting and determine a sample reaction rate parameter from the plurality of digital fluorescence sample data values. The data fitting may be a linear regression and the sample reaction rate parameter may correspond to a slope of a line generated by the linear regression. In other exemplary embodiments, the data fitting may be exponential and the sample reaction rate parameter may correspond to an exponent. In other exemplary embodiments, the data fitting may also be logarithmic or have both linear and saturation components, for example.

The processor further may determine the analyte concentration from a comparison of the sample reaction rate parameter with the calibration data stored in the memory. The processor also may determine a plurality of moving averages from the plurality of digital fluorescence sample data values, and perform the data fitting using the plurality of moving averages to determine the sample reaction rate parameter.

In an exemplary embodiment, the processor further is to determine the calibration data. The processor may compare the sample reaction rate parameter to linearized calibration data generated from determining a plurality of reaction rates from a corresponding plurality of calibration samples having known analyte concentrations. In another exemplary embodiment, the processor also may interpolate the calibration data using the sample reaction rate parameter to determine the analyte concentration.

In various exemplary embodiments, the processor may determine the calibration data by performing a first data fitting and determining a first or next calibration sample reaction rate parameter from the plurality of digital fluorescence sample data values corresponding to the first or next known analyte concentration, generating a plurality of calibration sample reaction rate parameters corresponding to a plurality of different known analyte concentrations, and performing a second data fitting, such as a linear regression, using the plurality of calibration sample reaction rate parameters to generate the calibration data. Also in various exemplary embodiments, the processor may determine site-specific calibration data by generating an offset factor for multiplication with the calibration data. For example, the processor may determine the offset factor by comparing data from a first site sample with data from a second site sample having an addition of a known amount of analyte.

In various exemplary embodiments, the user interface further comprises a visual display; and a keypad. The processor may provide the analyte concentration for display on the visual display of the user interface.

In an exemplary embodiment, the system may further comprise the cuvette, wherein the cuvette has a plurality of substantially flat, rectangular sides. Two opposing sides of the cuvette may be recessed and two opposing sides of the cuvette may be non-recessed, wherein the sensing chamber further comprises at least one extension or flange which blocks at least one of the non-recessed sides and prevents seating of the cuvette in the sensing chamber.

In various exemplary embodiments, the light source comprises: a light emitting diode to generate the light; a first bandpass filter; and a first lens to focus the light on an interior center of the cuvette. An exemplary system and apparatus may further comprise: a second lens to collect the fluorescence signal from the interior center of the cuvette, the second lens arranged substantially at a right angle to the first lens; and a second bandpass filter.

An exemplary fluorimetric system may further comprise an input/output interface disposed on the exterior of the apparatus housing and coupled to the processor, such as a USB driver and port or an Ethernet driver and port.

In an exemplary embodiment, the apparatus housing has a size adapted to fit into a user's hand, and the system is portable and operative in field use. The apparatus housing may further comprise a plurality of substantially optically non-reflective surfaces. The apparatus housing may further comprise a polymer shell structure comprising two parts and a polymer or rubber sealing O-ring disposed about an interior of an interface between the two parts.

In various exemplary embodiments, the outer light baffle comprises an elongated rim of the sensing chamber cover and a mating recess in the apparatus housing; and the inner light baffle comprises a protruding inner ring structure of the sensing chamber cover and a mating recess in the apparatus housing.

Also in various exemplary embodiments, the lowest detectable analyte concentration is in the parts per billion range. In addition, in exemplary embodiments, the sensor reagent housing is single-use.

An exemplary method of measuring an analyte concentration in a sample is also disclosed, with the method comprising: mixing the sample with a nucleic acid-based reagent having a fluorophore to generate a fluorescence signal; sampling an amplified fluorescence signal and generating a plurality of digital fluorescence sample data values; using a processor, performing a data fitting and determining a sample reaction rate parameter from the plurality of digital fluorescence sample data values; and using the processor, determining the analyte concentration from a comparison of the sample reaction rate parameter with calibration data stored in a memory. The data fitting may be a linear regression and the sample reaction rate parameter may correspond to a slope of a line generated by the linear regression. In another exemplary embodiment, the data fitting may be exponential and the sample reaction rate parameter may correspond to an exponent.

An exemplary method may further comprise, using the processor, determining the calibration data. For example, the method may determine the calibration data by: (a) mixing a calibration sample having a first or next known analyte concentration with a nucleic acid-based analysis chemistry reagent having a fluorophore to generate a first or next calibration fluorescence signal; (b) sampling a first or next amplified fluorescence signal and generating a plurality of digital fluorescence sample data values corresponding to the first or next known analyte concentration; (c) using the processor, performing a first data fitting and determining a first or next calibration sample reaction rate parameter from the plurality of digital fluorescence sample data values corresponding to the first or next known analyte concentration; (d) repeating steps (a) through (c) to generate a plurality of calibration sample reaction rate parameters corresponding to a plurality of different known analyte concentrations; and (e) using the processor, performing a second data fitting using the plurality of calibration sample reaction rate parameters to generate the calibration data. In an exemplary embodiment, the method may further comprise, using the processor, determining site-specific calibration data by generating an offset factor for multiplication with the calibration data, and determining the offset factor by comparing data from a first site sample with data from a second site sample having an addition of a known amount of analyte.

In an exemplary embodiment, the comparison step may further comprise, using a processor and the sample reaction rate parameter, comparing the sample reaction rate parameter to linearized calibration data generated from determining a plurality of reaction rate parameters from a corresponding plurality of calibration samples having known analyte concentrations. In various exemplary embodiments, the comparison step may further comprise, using the processor and the sample reaction rate, interpolating the calibration data to determine the analyte concentration. The exemplary method may further comprise, using a processor, determining a plurality of moving averages from the plurality of digital fluorescence sample data values; and wherein the step of performing the data fitting further comprises performing the data fitting using the plurality of moving averages.

In various exemplary embodiments, the mixing step may further comprise: injecting the sample through a sensor reagent housing having a channel and a porous medium in the channel, the porous medium having one or more nucleic acid analysis chemistry reagents; and collecting the mixture of the sample and the one or more nucleic acid analysis chemistry reagents in a cuvette. In an exemplary embodiment, the method may further comprise initiating the sampling step through a user interface, and using the processor, displaying the analyte concentration on a user interface.

In another exemplary embodiment, the method may further comprise detecting the fluorescence signal using a photomultiplier tube to generate a corresponding analog voltage level; and amplifying the analog voltage level.

In another exemplary embodiment, the method may further comprise preconditioning the sample, such as mixing the sample with a biological buffer and a salt.

Another exemplary embodiment provides an apparatus to determine an analyte concentration in a sample, with the apparatus comprising: an apparatus housing; a sensing chamber arranged to hold a cuvette; a sensing chamber cover movably coupled to the apparatus housing, the sensing chamber cover and apparatus housing together forming an inner light baffle and an outer light baffle over and around an upper portion of the sensing chamber; a user interface on an exterior of the apparatus housing; a light source in an interior of the apparatus housing in optical communication with the sensing chamber to provide light to the sensing chamber; a photomultiplier tube in the interior of the apparatus housing in optical communication with the sensing chamber to receive a fluorescence signal from the sensing chamber and generate a corresponding fluorescence voltage signal; an amplifier in the interior of the apparatus housing and coupled to the photomultiplier tube to amplify the fluorescence voltage signal; an analog-to-digital converter in the interior of the apparatus housing and coupled to the amplifier to generate a plurality of digital fluorescence sample data values in response to the amplified fluorescence voltage signal; a memory in the interior of the apparatus housing, the memory to store calibration data; and a processor in the interior of the apparatus housing and coupled to the memory and to the analog-to-digital converter to receive the digital fluorescence sample data values and to determine an analyte concentration of the sample.

Another exemplary embodiment provides a portable apparatus to measure an analyte concentration in a sample in field use, with the apparatus comprising: an apparatus housing having a size adapted to fit into a user's hand and comprising a plurality of substantially optically non-reflective surfaces; a sensing chamber within the housing and arranged to hold a cuvette; a sensing chamber cover movably coupled to the apparatus housing, the sensing chamber cover and apparatus housing together forming an inner light baffle and an outer light baffle over and around an upper portion of the sensing chamber; a user interface comprising a visual display and a keypad; a USB input/output interface; a light source in optical communication with the sensing chamber to provide light to the sensing chamber; a photomultiplier tube in optical communication with the sensing chamber to receive a fluorescence signal from the sensing chamber and generate a corresponding fluorescence voltage signal; an amplifier in the interior of the apparatus housing and coupled to the photomultiplier tube to amplify the fluorescence voltage signal; an analog-to-digital converter in the interior of the apparatus housing and coupled to the amplifier to generate a plurality of digital fluorescence sample data values in response to the amplified fluorescence voltage signal; a memory in the interior of the apparatus housing, the memory to store general calibration data and a site-specific offset factor; and a processor coupled to the memory, to the USB input/output interface, and to the analog-to-digital converter to receive the digital fluorescence sample data values, to determine a plurality of moving averages from the plurality of digital fluorescence sample data values, to perform a linear regression data fitting of the plurality of moving averages, to determine a sample reaction rate parameter from the linear regression, to modify the calibration data by the offset factor, to determine the analyte concentration from a comparison of the sample reaction rate parameter with the modified calibration data, and to provide the analyte concentration for display on the visual display of the user interface.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. (or "FIG.") 1 is a first perspective view illustrating an exemplary apparatus embodiment.

Figure 1:
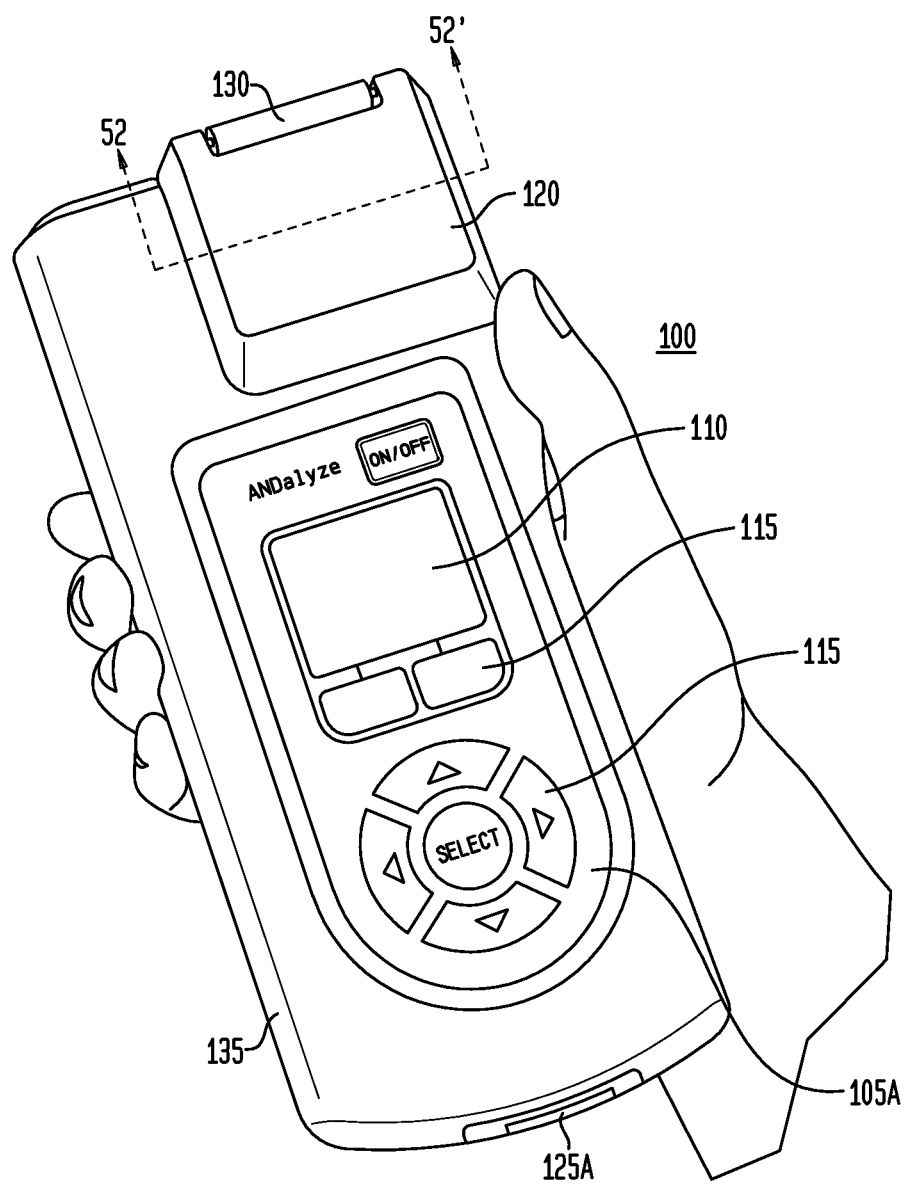

FIG. (or "FIG.") 2 is a second perspective view illustrating an exemplary apparatus embodiment.

FIG. (or "FIG.") 3 is a perspective view illustrating an exemplary system embodiment.

FIG. (or "FIG.") 4 is a perspective view illustrating exemplary sensor reagent housing component embodiments.

FIG. (or "FIG.") 5 is a perspective view illustrating an exemplary assembled sensor reagent housing embodiment.

FIG. (or "FIG.") 6 is a perspective view illustrating an exemplary cuvette embodiment.

FIG. (or "FIG.") 7 is a cross-sectional view illustrating an exemplary cuvette embodiment.

FIG. (or "FIG.") 8 is a cross-sectional view illustrating an exemplary syringe, sensor reagent housing, cuvette, and a portion of the apparatus housing.

FIG. (or "FIG.") 9 is a block diagram illustrating exemplary components of the apparatus embodiment.

FIG. (or "FIG.") 10 is a graphical diagram illustrating an exemplary linear calibration and concentration detection.

FIG. (or "FIG.") 11 is a graphical diagram illustrating an exemplary concentration detection linear fitting.

FIG. (or "FIG.") 12 is a graphical diagram illustrating an exemplary concentration detection exponential fitting.

FIG. (or "FIG.") 13 is a graphical diagram illustrating an exemplary concentration detection logarithmic fitting.

FIG. (or "FIG.") 14 is a graphical diagram illustrating an exemplary concentration detection linear and saturation fitting.

FIG. (or "FIG.") 15 is a screen image of a user interface display for initiation of sample analysis.

FIG. (or "FIG.") 16 is a screen image of a user interface display for displayed results of a completed sample analysis.

FIG. (or "FIG.") 17 is a screen image of a user interface display for an initiation of a calibration process for lead.

FIG. (or "FIG.") 18 is a screen image of a user interface display for an initiation of a site calibration process for a new site.

FIG. (or "FIG.") 19 is a screen image of a user interface display for an entry of new site information for a site calibration process.

FIG. (or "FIG.") 20 is a screen image of a user interface display for a site calibration process for lead using a site water sample with an addition of a known amount of lead.

FIG. (or "FIG.") 21 is a screen image of a user interface display for a site calibration process for lead using a site water sample.

FIG. (or "FIG.") 22 is a screen image of a user interface display for displayed results of a completed site calibration.

FIG. (or "FIG.") 23 is a cross-sectional view illustrating an exemplary sensor chamber cover, sensor chamber, cuvette, and a portion of the apparatus housing.

FIG. (or "FIG.") 24 is a flow chart illustrating an exemplary general calibration method embodiment.

FIG. (or "FIG.") 25 is a flow chart illustrating an exemplary site calibration method embodiment.

FIG. (or "FIG.") 26 is a flow chart illustrating an exemplary concentration detection method embodiment.

DETAILED DESCRIPTION OF EXEMPLARY EMBODIMENTS

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

Exemplary embodiments of the invention provide an apparatus, method and system for highly-sensitive detection of heavy metal ion concentrations using exemplary nucleic acid-based fluorimetry. Concentrations of ions such as lead, uranium, copper, mercury, cadmium, silver, etc., may be detected as low as a parts per billion (ppb) level, using just several user-friendly steps. One or more exemplary nucleic acid-based analysis chemistry reagents (as defined below) for the fluorimetric sensing is utilized herein (and referred to herein generally depending on the context as "analysis chemistry reagents", "sensor reagents", and more specifically as "nucleic acid-based analysis chemistry reagents" or "nucleic acid-based sensor reagents"). As discussed in greater detail below, such analysis chemistry reagents are or have been dried onto a frit 190 in a housing 200, which is therefore referred to as a "sensor reagent" housing 200, in the interests of brevity. Such analysis chemistry (or sensor) reagents may include a nucleic acid or nucleic acid enzyme. Examples of useful analysis chemistry (or sensor) reagents can be found in U.S. Patent Application Publication, Pub. No. 2007/0269821, entitled "LATERAL FLOW DEVICES" to Mazumdar et al.; U.S. Pat. No. 6,706,474, entitled "NUCLEIC ACID ENZYME BIOSENSORS FOR IONS" to Lu et al.; U.S. Pat. No. 6,890,719, entitled "FLUORESCENCE BASED BIOSENSOR" to Lu et al.; International Publication Number WO 2009/012309, entitled "NUCLEIC ACID BASED FLUORESCENT SENSOR FOR COPPER DETECTION" to Lu et al.; International Publication Number WO 2009/045632, entitled "NUCLEIC ACID BASED FLUORESCENT SENSOR FOR MERCURY DETECTION" to Lu et al.; and U.S. Patent Application Publication, Pub. No. 2010/0151579, entitled "FLUORESCENT SENSOR FOR MERCURY" to Wang et al., all of which are hereby incorporated by reference with the same full force and effect as if set forth in their entireties herein. The analysis chemistry (or sensor) reagents of these examples contain polynuclotides, such as nucleic acid enzymes, aptamers, aptazymes, and/or substrates; fluorophors; and quenchers. The visualization species and labels are fluorescent. U.S. Pat. No. 6,890,719 (noted above) describes analysis chemistry reagents including a nucleic acid enzyme and a substrate for the nucleic acid enzyme, each having a quencher, with one having a fluorophore. Other examples of useful analysis chemistry reagents are described in U.S. Patent Application Publication, Pub. No. 2006/0094026, entitled "NUCLEIC ACID ENZYME LIGHT-UP SENSOR UTILIZING INVASIVE DNA" to Lu et al.; and U.S. Patent Application Publication, Pub. No. 2007/0037171, entitled "APTAMER-BASED COLORIMETRIC SENSOR SYSTEMS" to Lu et al, both of which are also hereby incorporated by reference with the same full force and effect as if set forth in their entireties herein. These latter examples contain particles, and produce visualization species and labels that are colored. Other relevant U.S. Patents and Patent Application Publications, include without limitation, U.S. Pat. Nos. 7,192,708; 7,332,283; 7,534,560; and 7,485,419. On or about Jul. 15, 2010, the apparatus 100, system 300, and sensor kits are or will be available from ANDalyze, Inc. of Champaign, Ill., US (www.andalyze.com). Any other types of chemical reactions also may be utilized which result in fluorescence which may then be detected using the exemplary apparatus 100 and system 300, which provide a general platform for sensing any type of fluorescence for detection of any corresponding substance, in addition to the exemplary detection of heavy metal ions using the exemplary nucleic acid-based reagents, which therefore should not be regarded as limiting.

The following definitions are included to provide a clear and consistent understanding of the specification and claims.

The term "sample" is defined as a composition suspected of containing the analyte of interest that will be subjected to analysis. Typically, a sample for analysis is in liquid form, or can be converted into liquid form, and preferably the sample is an aqueous composition. A sample may be from any source, such as an industrial sample from a waste stream, or a biological sample such as blood, urine or saliva. A sample may be treated, such as by extract, dilution or filtration, or it may be a reconstituted precipitate from an industrial or biological source.

The term "analyte" is defined as one or more substances potentially present in a sample, for which the analysis tests. An analysis for an analyte determines the presence, quantity or concentration, of the analyte in the sample.

The terms "analysis chemistry reagents" or "sensor reagents" refers to one or more reagents, that when reacted with a sample containing an analyte, produce a visualization species. Preferably, the visualization species is produced in proportion to the amount or concentration of the analyte. Analysis chemistry reagents (and/or sensor reagents) preferably include a reactor and a substrate. The "reactor" is at least one compound, moiety and/or material; the "substrate" is also at least one compound, moiety and/or material. When the reactor and the substrate are mixed with the analyte, they will react to produce a visualization species. As used herein, the term "produce" includes forming by chemical reaction, as well as releasing from being bound or attached to something else. Preferably, the reactor is specific for an analyte, and the substrate is specific for a reactor. Preferably, the substrate includes a label. The reactor and the substrate may be attached, for example covalently or by hydrogen bonding (hybridization).

The term "visualization species" is a compound, moiety or material that can be detected, such as a fluorescent compound or a colored compound. A visualization species includes a label, which is that part of the visualization species that allows for detection, for example a colored label (such as a dye or a colored particle, including semiconductor nanoparticles (quantum dots)) or a fluorescent label (such as fluorescent compound). Preferably, the label of the visualization species originated as the label of the substrate. It is possible for the visualization species and the substrate to be the same.

The term "specifically bind" means that binding between the two things is more favored binding, as compared to most other members of the same class or genus. For example, the binding between an antibody specific for an antigen, and the antigen; and hybridization between two complementary strands of DNA; are both examples of specific binding.

The term "aptamer" refers to nucleic acid that specifically binds a target compound or moiety. The term "nucleic acid enzyme" (NAE) refers to nucleic acid that catalyses a chemical reaction (such as cleavage of a substrate) when it binds a specific cofactor (such as a divalent metal ion). Both an aptamer and a nucleic acid enzyme are examples of reactors.

The term "conformational change" refers to the process by which a nucleic acid, such as an aptamer, adopts a different secondary or tertiary structure. The term "fold" may be substituted for conformational change.

Figure 2:
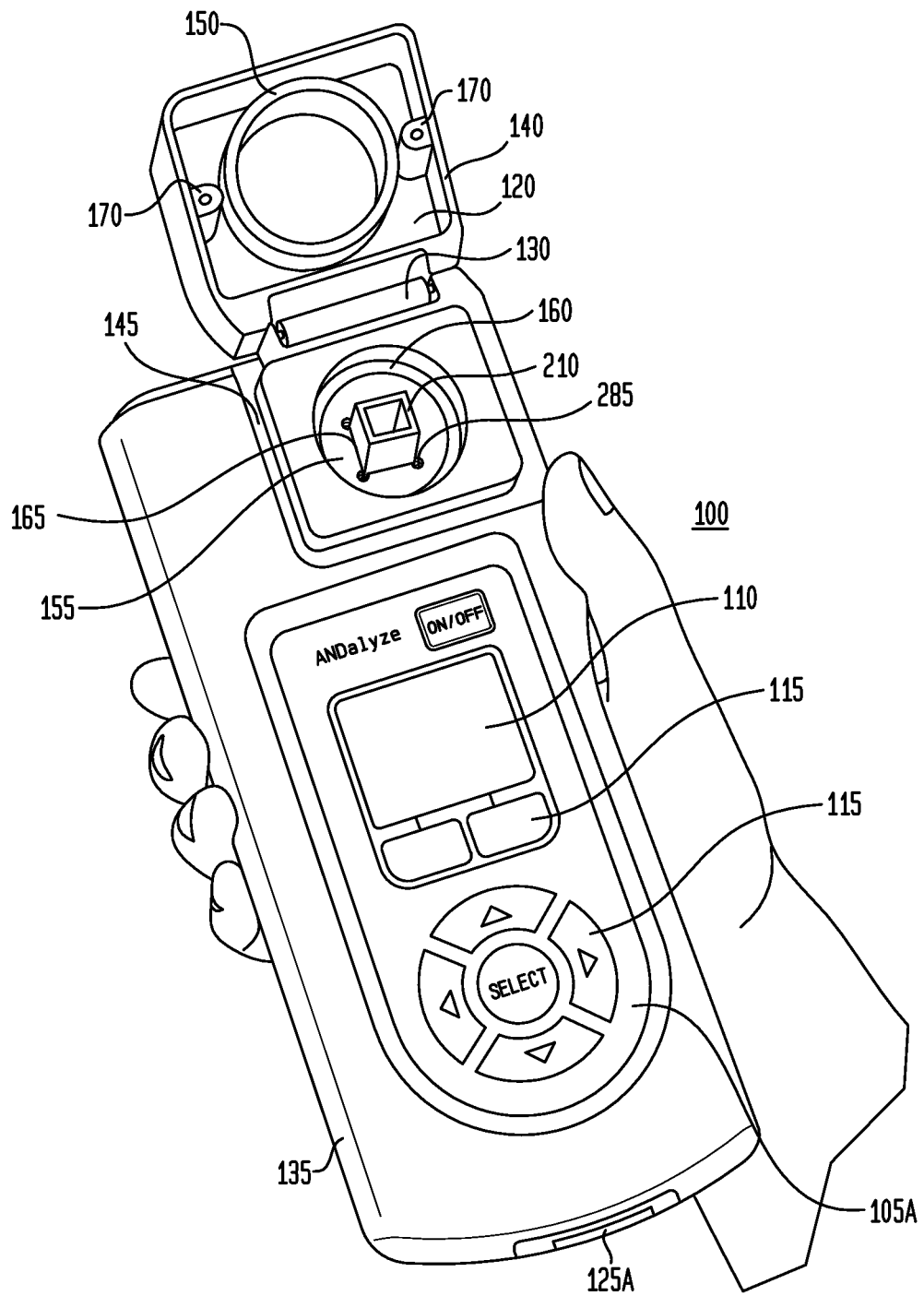
Figure 3:
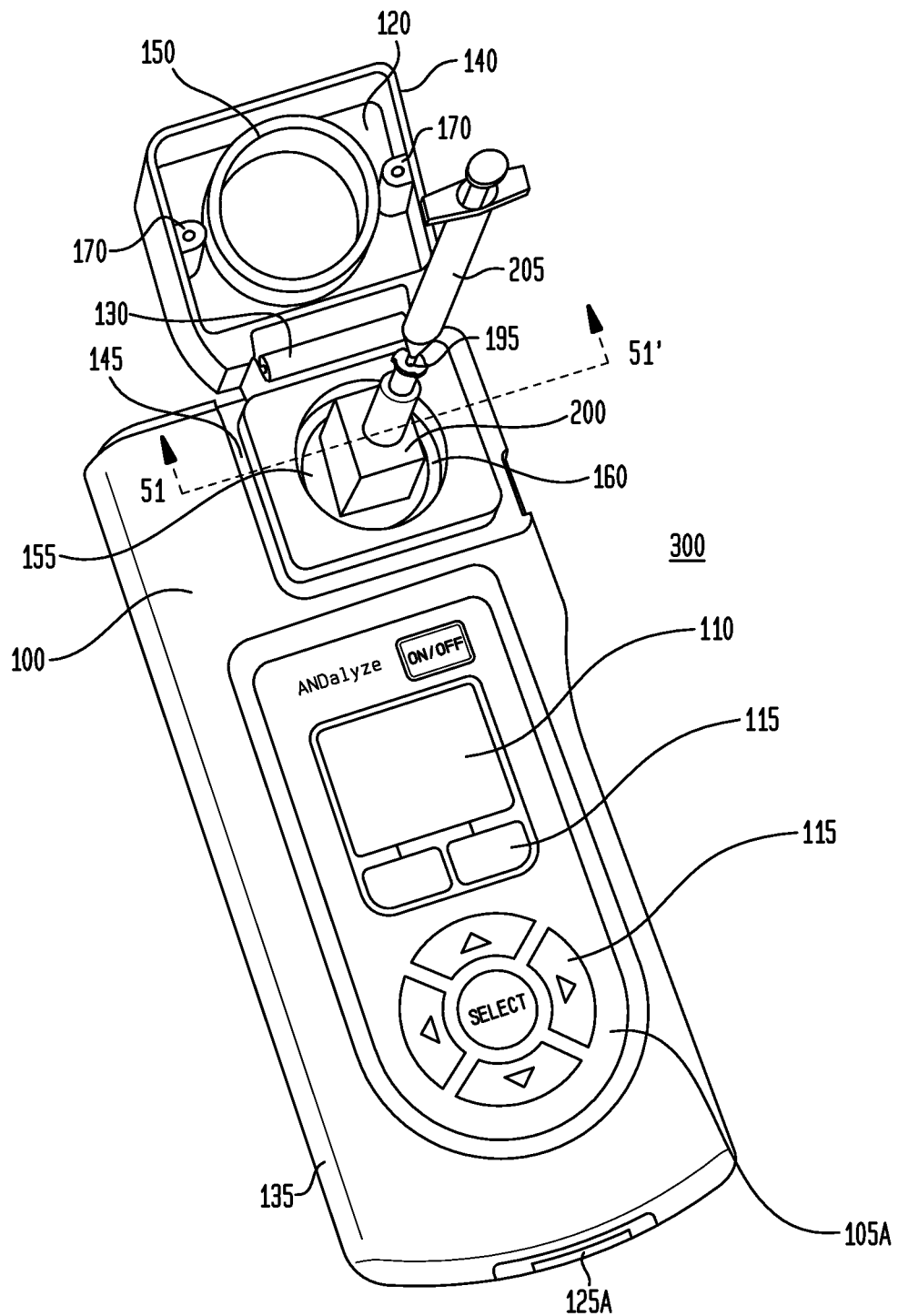

FIG. 1 is a first perspective view illustrating an exemplary fluorimeter apparatus 100 embodiment. FIG. 2 is a second perspective view illustrating an exemplary fluorimeter apparatus 100 embodiment with the sensing chamber cover 120 in an open position to illustrate the sensing chamber 90 having a cuvette 210 inserted therein. FIG. 3 is a perspective view illustrating an exemplary system 300 embodiment, illustrating an apparatus 100 in use with a syringe 205 and a sensor reagent housing 200 (coupled over a cuvette 210 within the sensing chamber 90, which is therefore not visible in FIG. 3).

Referring to FIGS. 1 and 2, the apparatus 100 comprises a housing 135, a user interface 105 (illustrated in the FIGS. 1-3 as a more specific user interface 105A embodiment having a display 110 and keypad 115), a sensing chamber 90 having a movable sensing chamber cover 120 (which, as illustrated, is pivotable about a hinge 130 into open and closed positions), and within the interior of the housing 135 (and therefore not illustrated in FIGS. 1-3), additional sensor components which are illustrated and discussed with reference to FIG. 9. Optionally, the apparatus 100 may include an additional input/output ("I/O") interface 125, illustrated in FIGS. 1-3 as I/O interface 125A embodied as a USB driver and port, as an example. Not separately illustrated, the apparatus 100 contains a power supply disposed or arranged within the housing 135, such as one or more batteries or power converter, as known in the art. Additional optional components, such as an interior sealing O ring 365 and other seals, are discussed below.

As described in greater detail below, the apparatus 100 is periodically calibrated prior to use, using reference samples having known concentrations of the selected type of analyte, which may also be followed by a site-specific calibration. For example, the apparatus 100 is calibrated in advance of first testing use, and then recalibrated after every fifty or one hundred subsequent testing uses. A site calibration may also be utilized, to accommodate or account for other agents which may be present in a site sample and which may affect fluorescence detection. Referring to FIGS. 1-3, as a general overview of system 300 operation, a syringe 205 contains the sample to be tested to determine its concentration of the selected analyte. The test sample is then injected through the sensor reagent housing 200, which contains the analysis chemistry reagents which have been dried onto a reagent frit 190. As the sample is injected, the sample at least partially re-hydrates and reacts with the analysis chemistry reagents held by the reagent frit 190 (illustrated in FIGS. 4 and 8), with the resulting mixture collected in a optically translucent or transparent cuvette 210 (illustrated in FIG. 6) which is held within the sensing chamber 90. The sensor reagent housing 200 and syringe 205 are then removed, the sensing chamber cover 120 is closed with the cuvette 210 within the sensing chamber 90, and as initiated by the user through the user interface 105A, the apparatus 100 detects or senses the concentration (if any) of the selected analyte, such as a heavy metal ion. The resulting analyte concentration is then displayed on the display 110 of the user interface 105A, and also may be downloaded to a computer or network (not separately illustrated) through the input/output ("I/O") interface 125, 125A and/or stored in a memory 310 (illustrated in FIG. 9).

The reagent frit 190 contains dried reagents such as nucleic acid-based analysis chemistry reagents or other analysis chemistry reagents. Such analysis chemistry reagents may include a nucleic acid or nucleic acid enzyme. Examples of useful analysis chemistry reagents can be found in Table I of U.S. App. No. 2007/0269821 A1, and in the other patents and publications described above. In an exemplary embodiment, the nucleic acid-based analysis chemistry (sensor) reagent comprises a DNA enzyme hybridized with a substrate, with one having one or more fluorophores and the other having one or more quenching molecules or structures. An analyte such as a lead, mercury or uranium ion acts as a catalytic cofactor, such that when combined with the nucleic acid-based analysis chemistry reagent, a reaction of the enzyme and substrate is catalyzed, the substrate is cleaved and the fluorophore is no longer being quenched, resulting in fluorescence which may be detected by the apparatus 100. Depending upon the concentration of the analyte cofactor, the reaction rate is higher or lower. In this exemplary embodiment, using several different known concentrations of analyte (one at a time), the corresponding rates of reaction are detected by the fluorimetric apparatus 100, and through the calibration process, the reaction rates are (generally linearly) correlated with the corresponding known concentrations of analyte. The rate of reaction of the test sample may then be determined and compared with the calibrated rates of reaction to determine the (previously) unknown concentration of analyte in the test sample.

In an exemplary embodiment, the dried reagents include one or more saccharides, such as to preserve the analysis chemistry reagents. The saccharide may be any water-soluble saccharide, including monosaccharides such as mannose, fructose, or ribose; disaccharides such as trehalose, lactose, maltose, sucrose, or turanose; and/or polysaccharides such as hydroxyethylstarch, inulin, or dextran; or mixtures thereof. In an exemplary embodiment, the disaccharide trehalose is utilized. Other chemicals may be present in the dried reagents, such as a buffer or salts. The dried reagent should be protected from contact with skin, and should be kept dry before use. The dried reagents may be prepared by mixing one or more sugars, the analysis chemistry reagents, a buffer and salts, and then allowing the mixture to air dry on the frit 190. Vacuum and/or chemical desiccation may then be used to further dry the dried reagents and maintain them in a substantially dried form.

The apparatus 100 can be portable and configured to have a form factor suitable for being readily hand-held by the user, as illustrated in FIGS. 1 and 2. While other power sources may be utilized, as known in the art, the apparatus 100 may be battery powered (not separately illustrated), such as using a lithium polymer battery, enabling use in the field, such as for generally immediate detection of ion concentrations in lakes, ponds, marshes, streams, rivers, drinking water supplies, etc., in addition to use in a laboratory setting.

The apparatus 100 also has several additional unique features, such as first and second light baffles around the sensing chamber 90, O-ring and other light and water seals, to diminish or avoid potential interference with fluorescence detection by photomultiplier tube ("PMT") 325, as described in greater detail below.

Figure 4:
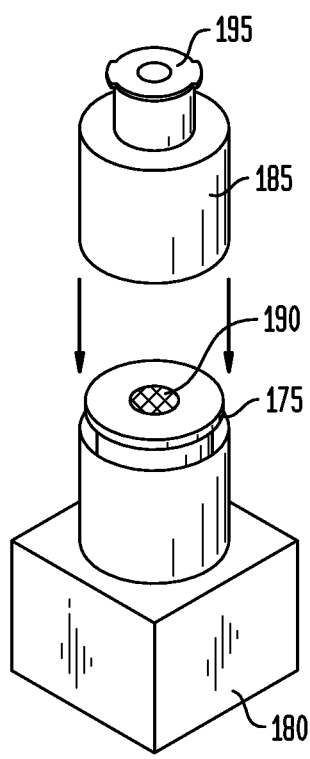
Figure 5:
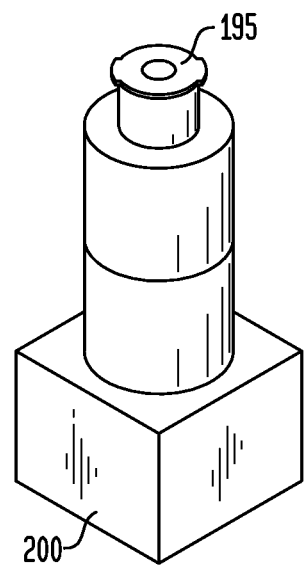
Figure 8:
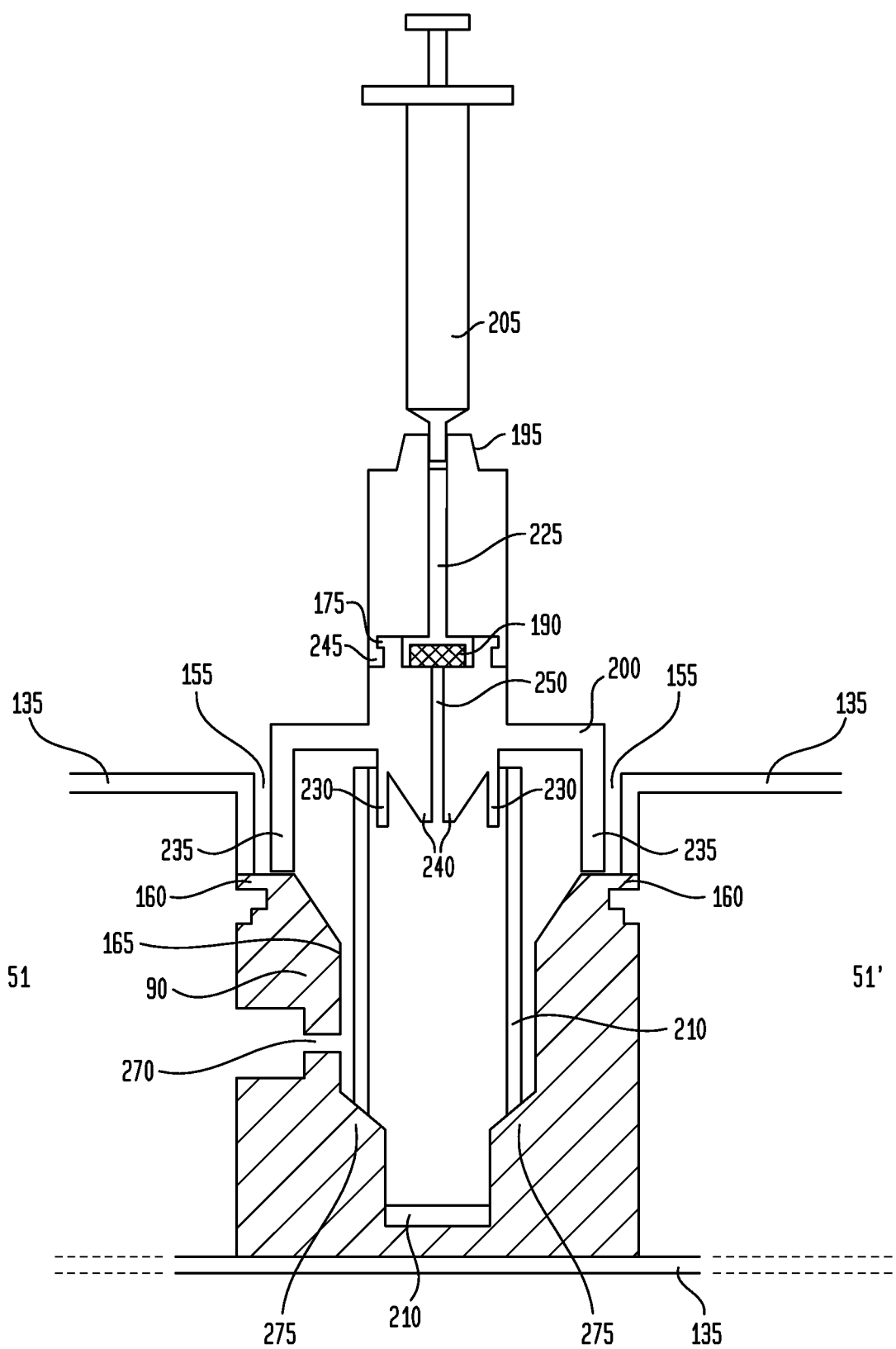

FIG. 4 is a perspective view illustrating exemplary sensor reagent housing 200 component embodiments. FIG. 5 is a perspective view illustrating an exemplary assembled sensor reagent housing 200 embodiment. Referring to FIG. 4, the sensor reagent housing 200 comprises a sensor reagent housing base 180, a reagent frit 190 having the sensor chemical(s), and sensor reagent housing top (or cap) 185. In an exemplary embodiment, the sensor reagent housing base 180 and sensor reagent housing top 185 are comprised of a durable and inert polymeric material, including, for example and without limitation, high-density polyethylene, low-density polyethylene, polypropylene, polycarbonate, polyethylene terephthalate, and polystyrene. Fabrication of the sensor reagent housing base 180 and sensor reagent housing top (or cap) 185 may be accomplished, for example, with injection molding. The reagent frit 190 is held in place in a recess or cavity between the sensor reagent housing base 180 and sensor reagent housing top 185 which, as illustrated are then coupled together (such as through interlocking (or snap) fittings 175, 245) to form a unitary sensor reagent housing 200, as illustrated in FIG. 5. Other mechanisms of holding the analysis chemistry reagents, and other mechanisms of joining or coupling the sensor reagent housing base 180 and sensor reagent housing top 185 will be readily apparent to those having skill in the art and are considered equivalent and within the scope of the disclosure. In an exemplary embodiment, the channel (or bore) 250 of the sensor reagent housing base 180 has a smaller diameter than the channel (or bore) 225 of the sensor reagent housing top (or cap) 185, which may serve to accelerate the fluid flow and aid in mixing the sample fluid with the analysis chemistry reagents. In addition, the sensor reagent housing top 185 further comprises a nozzle fitting 195, having a form and sized to securely and removably hold the nozzle portion of a syringe 205 during operation (as illustrated in FIGS. 3 and 8), as the sample is injected through the channel (or bore) 225, the reagent frit 190, and out of the channel (or bore) 250 of the housing 200 and into the cuvette 210, and further allowing release of the syringe 205 following sample injection. In an exemplary embodiment, sensor reagent housings 200 are color-coded to correspond to selected analytes, such as green for lead, orange for uranium, blue for copper, etc., with darker corresponding colors utilized for the sensor reagent housings 200 used in the corresponding calibration of the selected analyte.

Figure 6:
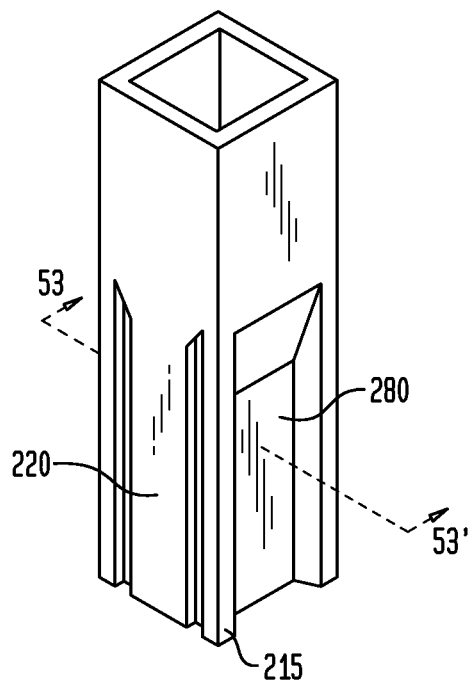
Figure 7:
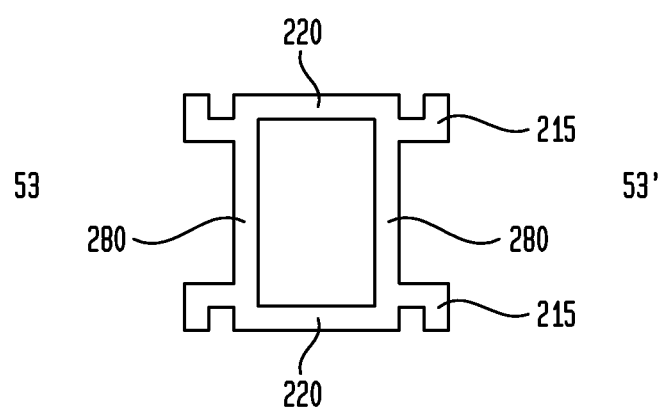

FIG. 6 is a perspective view illustrating an exemplary cuvette 210 embodiment. FIG. 7 is a cross-sectional view (through the 53-53' plane of FIG. 6) illustrating an exemplary cuvette 210 embodiment. The cuvette 210 is generally comprised of an optically clear or translucent material sufficient to allow energizing and detection of emitted fluorescence in a suitable or selected wavelength range during apparatus 100 operation, such as a polymethyl methacrylate (PMMA), a polycarbonate or a silica glass, for example. As illustrated, the cuvette 210 has a generally rectangular form, with flat sides 220, 280 which are perpendicular to the directions of entering (energizing) and emitted light, to avoid causing potentially interfering reflections, including internal reflections which may occur with curved cuvettes. In addition, the cuvette 210 is a "directional" cuvette having two recessed sides 280 on opposing sides of the cuvette 210, which are utilized to properly seat the cuvette 210 within the sensing chamber 90 (using mating extensions or flanges 275 extending into the sensing chamber 90 as illustrated in FIG. 8). In an exemplary embodiment, when the cuvette 210 is inserted into the sensing chamber 90 in a correct, first orientation, the recessed sides 280 provide sufficient clearance with the mating extensions or flanges 275, the cuvette 210 can be lowered fully into the sensing chamber 90 and the sensing chamber cover 120 can be closed. If the cuvette 210 is inserted into the sensing chamber 90 in a wrong, second orientation, however, the mating extensions or flanges 275 extending into the sensing chamber 90 (in corresponding areas of the bottom of the housing 135) prevent the cuvette 210 from being lowered fully (as the sides 220 are not recessed), the cuvette 210 is slightly raised and the sensing chamber cover 120 does not fully close, indicating that the cuvette 210 should be removed, rotated 90° (in the plane of the apparatus 210) and re-inserted in the proper, first orientation. In addition, cavities 285 in the sensing chamber 90 may also be utilized to provide directionality for orientation of flanges 215 of the cuvette 210 for insertion of the cuvette 210 into the sensing chamber 90 in the proper, first orientation. Those having skill in the art will recognize that additional flange or extension shapes may be utilized to provide such directionality and proper seating, in addition to the illustrated arrangement.

FIG. 8 is a cross-sectional view (through the 51-51' plane of the system 300 illustrated in FIG. 3) illustrating an exemplary syringe 205, sensor reagent housing 200, cuvette 210, the sensing chamber 90, and a portion of the apparatus housing 135. Referring to FIGS. 3 and 8, as illustrated, the nozzle of the syringe 205 is held by the nozzle fitting 195 of the sensor reagent housing 200, allowing injection of the syringe contents, namely the sample to be tested, generally about 1 ml, into the housing channel (or bore) 225, through the reagent frit 190, through the channel (or bore) 250 of the sensor reagent housing base 180, out of the housing nozzle 240, and into the cuvette 210 held in the sensing chamber 90 (within interior sensing chamber walls 165). Walls of the sensor reagent housing 200 (more particularly, of the sensor reagent housing base 180) are configured to fit around the walls of the cuvette 210 and secure the sensor reagent housing 200 in a proper location to allow collection of the mixture of the sample and analysis chemistry reagents to be collected in the cuvette 210. More particular, interior housing walls 230 are configured to fit within the interior of the cuvette 210, and exterior housing walls 235 are configured to fit around the exterior of the cuvette 210 and rest on top (160) of the sensing chamber 90, with the housing nozzle 240 then generally centered within the opening of the cuvette 210. In addition to the upper opening through which the cuvette 210 is inserted, the sensing chamber 90 has a first light path opening 270, for entry of an energizing light beam, and a second light path opening (not separately illustrated) at ninety degrees for the transmission of the fluorescence for detection. In an exemplary embodiment, the sensing chamber 90 is machined, molded or cast, and includes light path coupling or attachment mechanisms (not separately illustrated) for light reception and fluorescent emissions, to avoid interference from other potential light sources, and includes a cavity or void for insertion of a cuvette 210 as illustrated. In other embodiments, the sensing chamber also may be formed as part of the housing 135, for example and without limitation. Additional details and specifications of the sensor reagent housing 200, syringe 205 and cuvette 210 are described in the related application.

Figure 15:
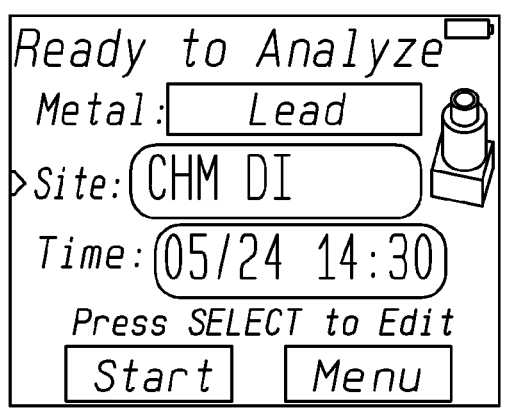

The reagent frit 190 typically comprises a porous material, such as a porous plastic media (e.g., polyethylene), having pore sizes in the range of 10 -50 microns, also serving to remove particulates in the sample. When polyethylene is utilized, the pore sizes are typically in the range of 15 -45 microns. The porous material of the frit 190 may have a lower melting or degradation temperature than sensor housing top and base 185, 180. As discussed in greater detail in the related application, the analysis chemistry reagents have been dried onto the reagent frit 190. During use, as the sample (or preconditioned sample) is injected through the channel (or bore) 225 of the sensor reagent housing 200, the analysis chemistry reagents are re-hydrated, with the resulting mixture of the sample and analysis chemistry reagents passing out of the channel (or bore) 250 and nozzle 240 held in the cuvette 210 for analysis. Depending upon the sample to be tested, additional sample pre-conditioning or preparation may be utilized in advance of sample injection, such as using an EPA protocol to obtain a sample of lead paint, or adding a buffering agent to adjust pH, for example. In an exemplary embodiment, a sample tube or calibration tube is supplied, which may contain pre-conditioning reagents or buffering chemicals in the form of a liquid, pellet or powder, such as biological buffers (e.g., MES, HEPES, TRIS, MOPS, etc.) and salts (for example, sodium chloride, potassium chloride, ammonium chloride, magnesium chloride, calcium chloride, etc.), to provide standardized level of water hardness and pH. The selection of pre-conditioning reagents will also typically depend on the analyte of interest (i.e., the preconditioning is "tuned" for the particular application); for example, a sample for lead will typically be preconditioned to have a pH of about 7, while a sample for uranium will typically be preconditioned to have a pH of about 5. The porous plastic media also acts a filter, depending on the pore size, preventing various particulates from entering the cuvette 210 and potentially interfering with subsequent optical measurements. Following injection of the sample, the sensor reagent housing 200 and syringe 205 are removed, the sensing chamber cover 120 is then closed over the sensing chamber 90 holding the cuvette 210 with the mixture of the sample, analysis chemistry reagents and any other pre-conditioning agents or chemicals, and analysis may be commenced by the user through the user interface 105, 105A, such as through keypad 115 entry of "Start" as shown on the displayed "Ready to Analyze" screen image of display 110 of FIG. 15.

It should be noted that each sensor reagent housing 200 (with its reagent frit 190), cuvette 210, and syringe 205 is designed for a single use, and may be disposed or recycled following such single use. A plurality of sensor reagent housings 200 may be purchased as part of a kit which also includes a plurality of sensor reagent housing 200 used for calibration, calibration samples having known concentrations of analyte, syringes, cuvettes 210, and various mixing tubes containing pre-conditioning reagents.

Figure 9:
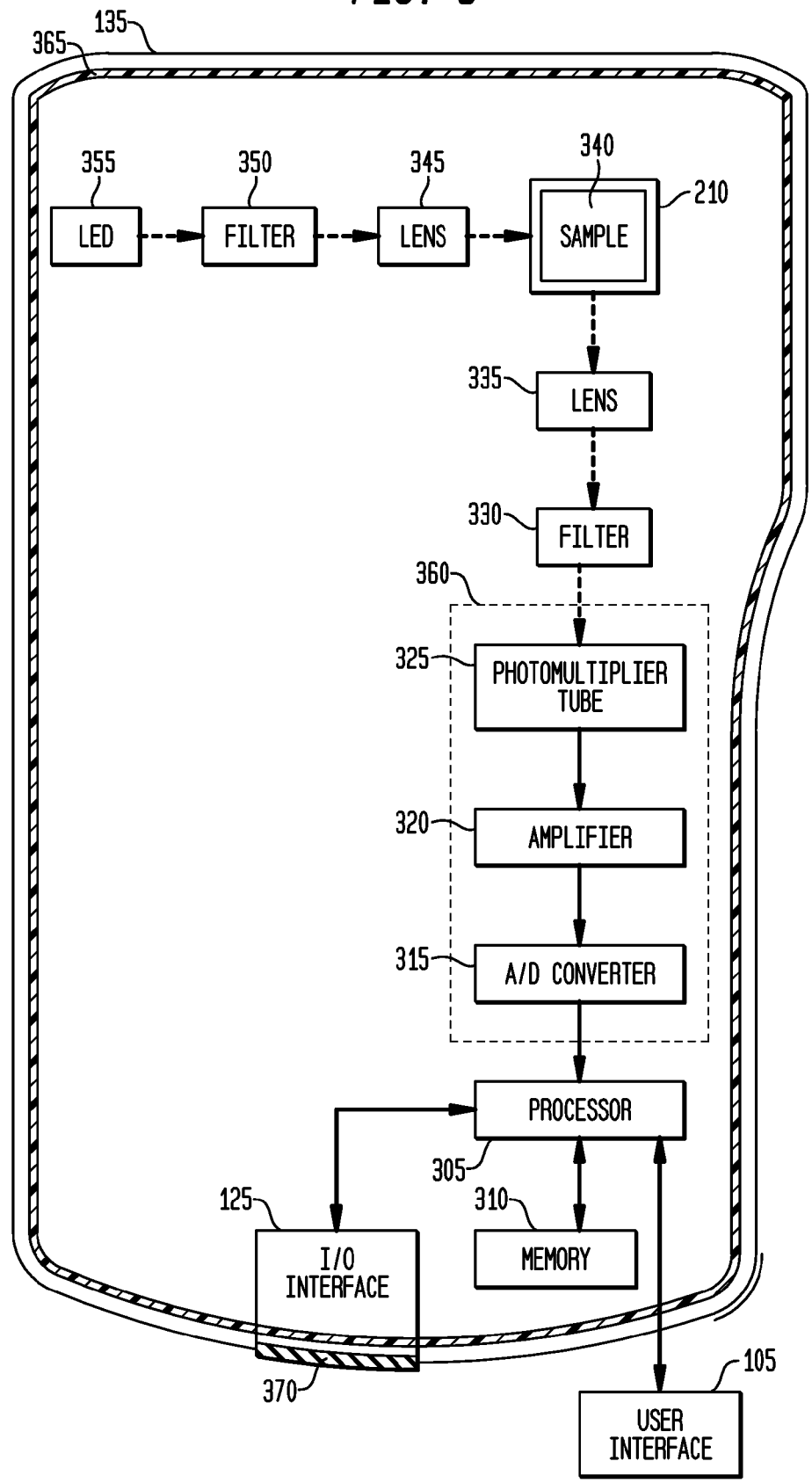

FIG. 9 is a block diagram illustrating exemplary components of the apparatus embodiment, utilized to provide energizing light and to detect emitted light (fluorescence) from the reaction of the analyte of the sample and the analysis chemistry reagents, to calculate the resulting concentration of analyte or calibrate based on a known concentration of analyte, and to output the results on the display 110 of the user interface 105, 105A and/or output the results (e.g., to a computer or communication network, not illustrated) via the I/O interface 125, 125A. A power supply, such as a battery, and power and ground wires or connections, are not separately illustrated, as such power supplies and power distribution are well known in the electronic arts. The dashed arrows of FIG. 9 are utilized to indicate optical, wireless connections, with the solid arrows utilized to indicate wired connections. While an exemplary layout of the exemplary components within the housing 135 is illustrated in FIG. 9 for ease of explanation, in an exemplary embodiment the components have a closely packed layout (including in 3D) to substantially minimize the size of the apparatus 100 for portability, and those having skill in the art will recognize that innumerable component layouts are available and within the scope of the disclosure With a calibration sample (mixed with analysis chemistry reagents) or test sample (mixed with analysis chemistry reagents and any other pre-conditioning agents or chemicals) in place in the cuvette 210, as initiated by a user through the user interface 105, 105A, and under the control of the processor 305, a light emitting diode ("LED") 355 is energized and generates light, providing an energizing light source, and the resulting light is filtered by optical filter 350 and focused by lens 345 to provide energy generally to the center of the sample 340 in the cuvette 210, generally at wavelengths in a band centered in the range of 485 nm. Resulting fluorescence is then detected at 90° from the source path, to avoid interference from the illumination source (LED 355). Using the lens 335 and optical bandgap filter 330, the fluorescence (typically emitted at wavelengths in a band centered in the range of about 518 nm) is respectively focused and filtered at wavelengths in a band centered in the range of about 530-535 nm, to reduce background noise and other interference, and is detected by a photomultiplier tube ("PMT") 325. An analog voltage output from the PMT 325 is amplified by amplifier 320 and sampled and converted into a fluorescence digital count value by analog-to-digital (A/D) converter 315, with the resulting fluorescence digital count value provided to the processor 305, which is typically implemented as a microprocessor in exemplary embodiments. As an option, the PMT 325, amplifier 315 and A/D converter 315 may be electromagnetically shielded by shielding 360, such as by using a metallic sheet, foil or tape, for example, also to reduce potential interference.

Figure 11:
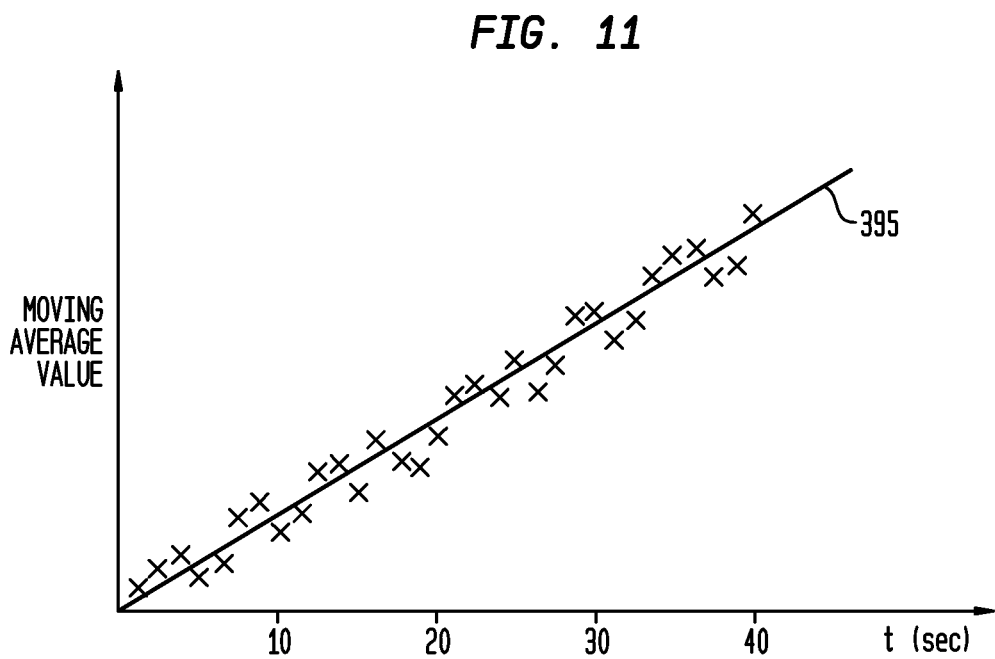

For each calibration or test sample, the A/D converter 315 typically samples the amplified analog voltage output from the PMT 325 about one hundred (or more) times over about forty seconds, to provide one hundred (or more) fluorescence digital count values, as one hundred corresponding sample points, to the processor 305. In other exemplary embodiments, the A/D converter 315 may output more fluorescence digital count values, and the processor 305 may be programmed to utilize any selected number of fluorescence digital count values as fluorescence sample points. As the digital fluorescence sample points are generated, the processor 305 calculates a moving average (indicative of "raw" fluorescence) using fifty sample points at a time, e.g., an average for sample points 1-50, an average for sample points 2-51, an average for sample points 3-52, etc., through an average for sample points 51-100. Using a linear regression as an example, with other, additional types of curve or data fitting analyses discussed below, a first linear equation is derived from the resulting averaged data samples (with the linear equation also forced to have a y-intercept of zero (using a Cartesian x-y coordinate system), illustrated as line 395 in FIG. 11, and the slope of the resulting first linear equation is calculated or otherwise determined by the processor 305, as one of the types of rate (or reaction rate) parameters which may be utilized herein (e.g., "m" is a rate parameter in a linear equation y=mx+b). The slope of the first linear equation, referred to herein as the "test sample reaction rate parameter" or the "calibration sample reaction rate parameter" (depending on whether testing or calibrating), is or represents a fluorescent count per unit time, and thereby provides an indication of the rate of the reaction of the analysis chemistry reagents as catalyzed by the analyte cofactor of the test sample or calibration sample, such as a nucleic acid-based sensor reagent using a lead ion cofactor.

Figure 12:
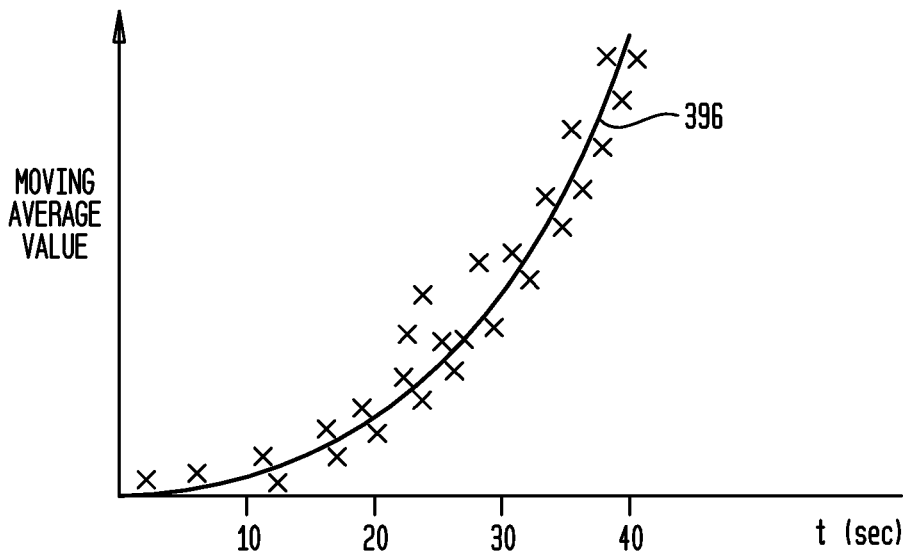
Figure 13:
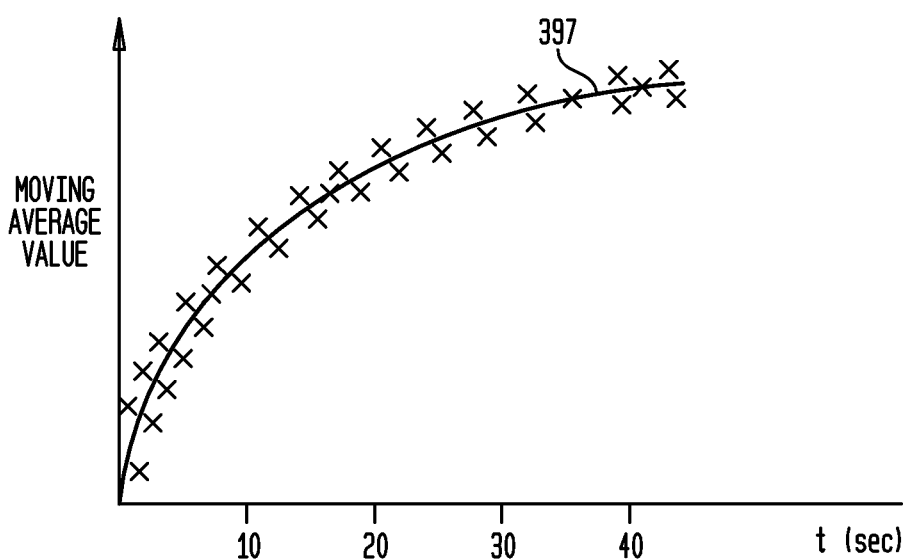
Figure 14:
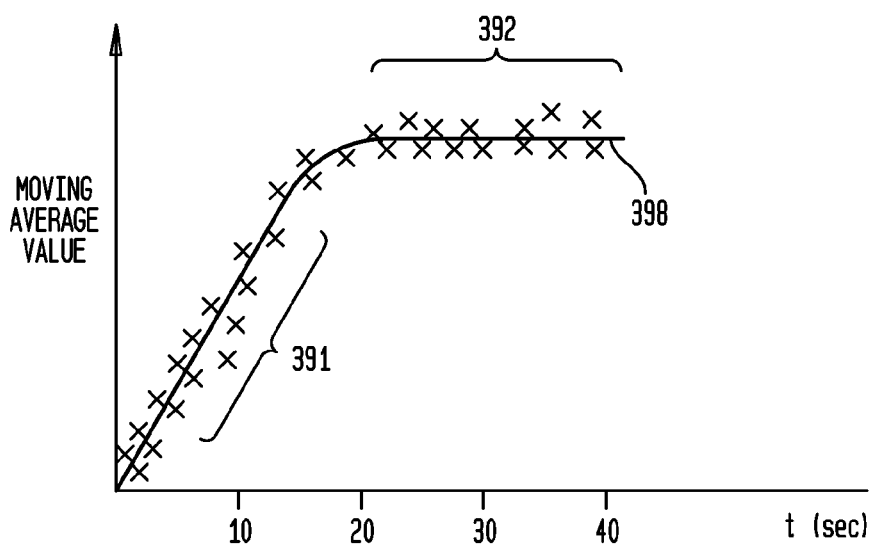

Exemplary embodiments of the apparatus 100 provide a dynamic or kinetic measurement, of multiple digital fluorescence samples over time, and the corresponding reaction rates may or may not be linear or otherwise within a linear range. For example, while lead ions may exhibit a substantially linear data fitting and resulting linear reaction rate parameter, other analytes such as mercury ions may exhibit a substantially exponential data fitting and resulting linear reaction rate parameter. In addition, the type of data fitting generally will also depend on the length of time over which sampling of the fluorescence occurs, as a shorter duration may provide a linear data fitting, while a longer duration may provide an exponential or a saturation data fitting, for example. Accordingly, in addition to a linear curve or data fitting analysis and a resulting linear reaction rate parameter, other types of curve or data fitting analyses and corresponding reaction rate parameters may also be determined and are within the scope of the disclosure. For example, the processor 310 may be programmed or configured (e.g., as a programmable microprocessor or a configurable FPGA) to perform a wide variety of curve or data fittings, such as exponential, logarithmic, linear, saturation, etc., and may do so dynamically, automatically providing a selected curve or data fitting based upon the current analysis results being obtained. FIG. 12 is a graphical diagram illustrating an exemplary concentration detection exponential data fitting, with exponential curve 396 and a resulting exponential reaction rate parameter (e.g., $k_1$ in an exponential equation $y=e^{-k_1 x}$). FIG. 13 is a graphical diagram illustrating an exemplary concentration detection logarithmic fitting, with logarithmic curve 397 and a resulting logarithmic reaction rate parameter (e.g., $k_2$ in a logarithmic equation $y=k_2 \log(x+1)$). FIG. 14 is a graphical diagram illustrating an exemplary concentration detection linear and saturation fitting, with curve 398 having a linear region 391 and a saturation region 392, such as for a resulting saturation reaction rate parameter (e.g., $k_3$ in a saturation equation $y \geq k_3 x$ for the saturation region 392) (typically utilized to detect a concentration which is greater than a predetermined level, e.g., 1000 ppb or higher).

Figure 10:
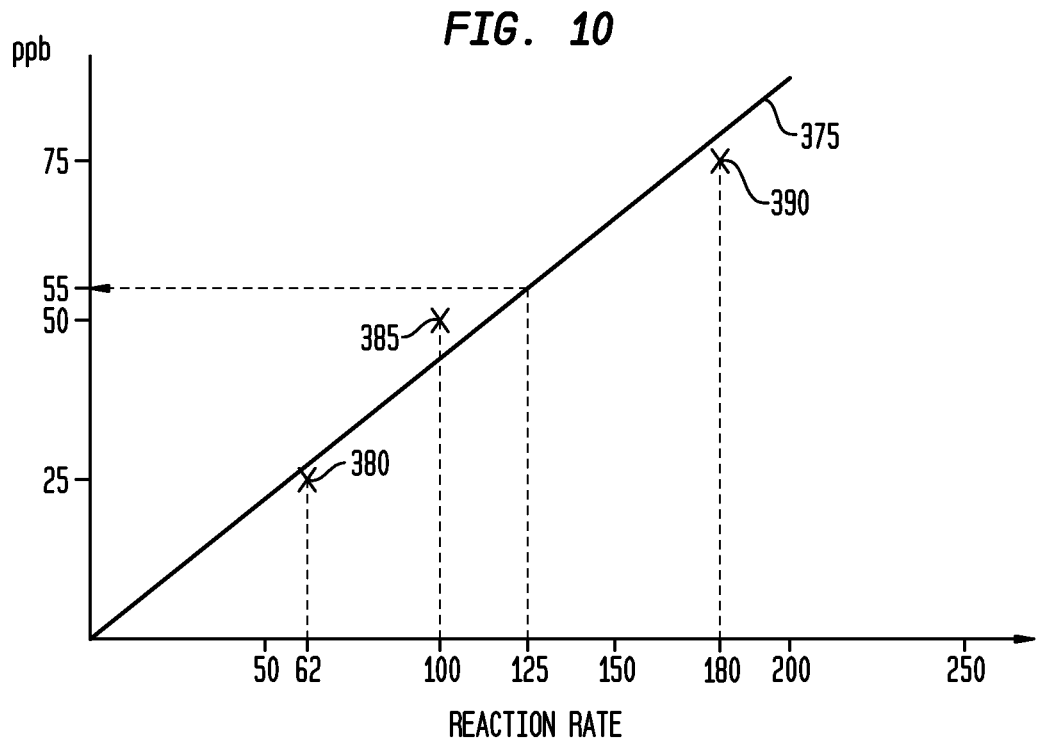

For a general or standard calibration of the apparatus 100 (i.e., which is not site-specific), this process is repeated at least three times using at least three different and known concentrations of analyte, such as twenty-five, fifty, and seventy-five ppb of lead, for example. Also for example, an initiation of this calibration process for lead is shown as the "Calibration" screen image of display 110 illustrated in FIG. 17. For each calibration sample concentration, one hundred fluorescence sample points (data) are determined and averaged and discussed above, a resulting curve or data fitting is calculated or otherwise determined by the processor 305, and corresponding reaction rate parameter is determined, such as determining the slope of the line 395 of FIG. 11 or exponential parameter for curve 396 of FIG. 12, also as discussed above. Exemplary reaction rates, as reaction rate parameter values, are illustrated in FIG. 10, such as a reaction rate parameter of 62 for 25 ppb, a reaction rate parameter of 100 for 50 ppb and a reaction rate parameter of 180 for 75 ppb. Using a second curve or data fitting analysis and the calibration reaction rate parameters, such as a linear regression analysis, a second curve or data fitting is determined (also by processor 305), such as a second linear equation, which is referred to as a calibration curve (or calibration data), with an exemplary linear calibration line illustrated as calibration line 375 in FIG. 10, and the (periodic) device calibration of the apparatus 100 is complete for the selected analyte. While illustrated in FIG. 10 as a linear calibration, other calibration curves are also within the scope of the disclosure, as discussed above, such as exponential, logarithmic, saturation, etc. In addition, samples may be conditioned (such as diluted), or the duration of reaction sampling reduced, to stay within a linear region (or piece-wise linear region) of an otherwise non-linear calibration. Calibration for a selected analyte is typically repeated after 50-100 testing analyses, to maintain accuracy under various environmental and other external conditions.

In addition, at any time following the general calibration, a second level of calibration may be performed which is site specific, to account for local or site-specific factors other than the analyte of interest, such as additional quenching which may occur from other agents in the sample to be tested which could potentially interfere with the analyte concentration determination. Such site-specific calibration generally will be repeated for each testing site, and the results may be stored in the apparatus 100. Site-specific calibration may begin with entry of site information into the apparatus 100, such as a site name or number, as shown in the screen images of FIGS. 18 and 19. Analysis is then performed using a site test sample and a known amount of analyte, such as lead. In an exemplary embodiment, a calibration tube is provided in which 20 ml of a site test sample and 1 ml of a 0.5 ppm analyte ion (such as lead) standard solution are mixed, with any appropriate preconditioning, followed by the analysis process discussed above, with initiation of the analysis shown on the screen image of FIG. 20. A second analysis is then performed with the apparatus 100 using just the site test sample (also with any appropriate preconditioning), as shown on the screen image of FIG. 21. The apparatus 100 then compares these site-specific results to the results which would otherwise have been expected from the general or standard device calibration and generates a multiplier or multiplicative "offset factor" (as shown in the screen image of FIG. 22), namely, a factor which the apparatus 100 will utilize to multiply with the standard device calibration data (e.g., to change the slope of the linear calibration curve 375) to then provide a site-specific calibration for analysis for that specific site only, and stores the site-specific offset factor in memory 310. Different sites may then have different offset factors or no offset factors, depending upon the individual, site-specific conditions or circumstances. For example, due to additional, site-specific quenching, an analysis from a first site may indicate 10 ppb of lead when it should indicate 20 ppb, resulting in an offset factor of "2" for use in analyses of test samples from that first site, while an analysis from a second site may indicate 50 ppb of lead when it should indicate 500 ppb, resulting in an offset factor of 10 for use in analyses of test samples from that second site, and conversely, an analysis from a third site may indicate 100 ppb of lead when it should indicate 50 ppb, resulting in an offset factor of 0.5 for use in analyses of test samples from that third site. In addition to multiplicative offset factors, other types of site-specific offset factors may be utilized, such as an additive offset factor, for example and without limitation.

Figure 16:
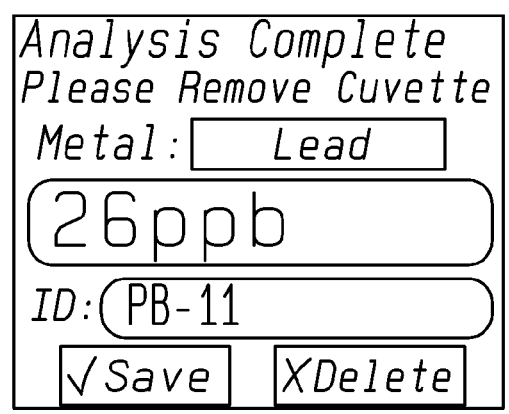

Following general calibration and any site-specific calibration for a selected analyte, the apparatus 100 may be utilized to determine concentrations of a selected analyte. For each sample of analyte to be analyzed, one hundred samples are determined and averaged and discussed above, a resulting first curve or data fitting is calculated or otherwise determined by the processor 305, and its reaction rate parameter is determined, such as determining the slope of the line 395 of FIG. 11, also as discussed above. The sample reaction rate parameter (illustrated as slope value "125" in FIG. 10 as an example) is input or fit to the calibration line 375 (stored in memory 310, and as may be modified by any offset factor) (illustrated in FIG. 10 without any offset), and from the corresponding point or datum of the calibration line or other calibration data, the resulting analyte concentration is determined, as illustrated in FIG. 10 as fifty-five ppb as an example. This determination is illustrated graphically by the dashed arrow of FIG. 10, using the corresponding slope (reaction rate) (in this case, "125" on the x-axis) of the test sample, comparing it to the calibration data (graphically illustrated as line 375), and obtaining the corresponding or correlated analyte concentration (graphically illustrated as "55" being read from the y-axis in FIG. 10). The resulting analyte concentration may then displayed to the user, such as on display 110 of user interface 105, 105A, output to another device or network via I/O interface 125, and/or stored in memory 310, such as for subsequent download, for example. As an example, an output of 26 ppb of lead is shown as the displayed results of the "Analysis Complete" screen image of display 110 illustrated in FIG. 16.

While not separately illustrated in FIGS. 15-22, additional screen images are also utilized for display on the display 110 of the user interface 105, 105A, such as to prompt the user to insert the different concentrations of calibration samples, and for other user interactive features, such as setting high or low limits (e.g., to simply determine whether the sample has an analyte in excess of an upper limit, rather than requiring an actual ppb numerical output), on-board diagnostics, sample averaging selections, etc., for example and without limitation. In addition, through the I/O interface 125, the apparatus 100 may be coupled to a computer having corresponding software, such as for recording data, exporting data to various other programs such as Excel, resetting the apparatus 100 to factory default settings, managing memory, internal testing and diagnostics, etc.

While illustrated graphically in FIGS. 10-14, those having skill in the art will recognize that such calibration, reaction rate parameter determinations, linear regression analyses, offset factors, etc., generally are determined digitally by the processor 305, with corresponding values stored in the memory 310. In addition, calibration values may be pre-populated in the memory 310, such as in the form of a look up table. For example, corresponding values for a plurality of calibration lines 375 and offset factors may be stored in memory 310, with the data corresponding to a selected calibration line 375 selected based on determinations from the calibration process describe above. The corresponding data for the selected calibration line 375 may then be utilized to provide the concentration results for a test sample, based on the reaction rate parameter (e.g., slope value) determined from the test sample, such as through interpolation or a look up table stored in memory 310, for example and without limitation.

As mentioned above, the apparatus 100 and system 300 provide detection sensitivity in the parts per billion range. Test samples having higher concentrations may be correspondingly diluted prior to testing, to maintain the catalyzed reaction in its linear (rather than saturation) range.

The LED 355, filters 350, 330, lenses 345, 335, PMT 325, amplifier 320, A/D converter 315, shielding 360, processor 305, memory 310, I/O interface 125, and user interface 105 may be implemented as known or becomes known in the electronic and optical arts. The various components may also be implemented as discrete or integrated components, for example and without limitation. The I/O interface 125, processor 305 and memory 310 are also described in greater detail below.

Figure 23:
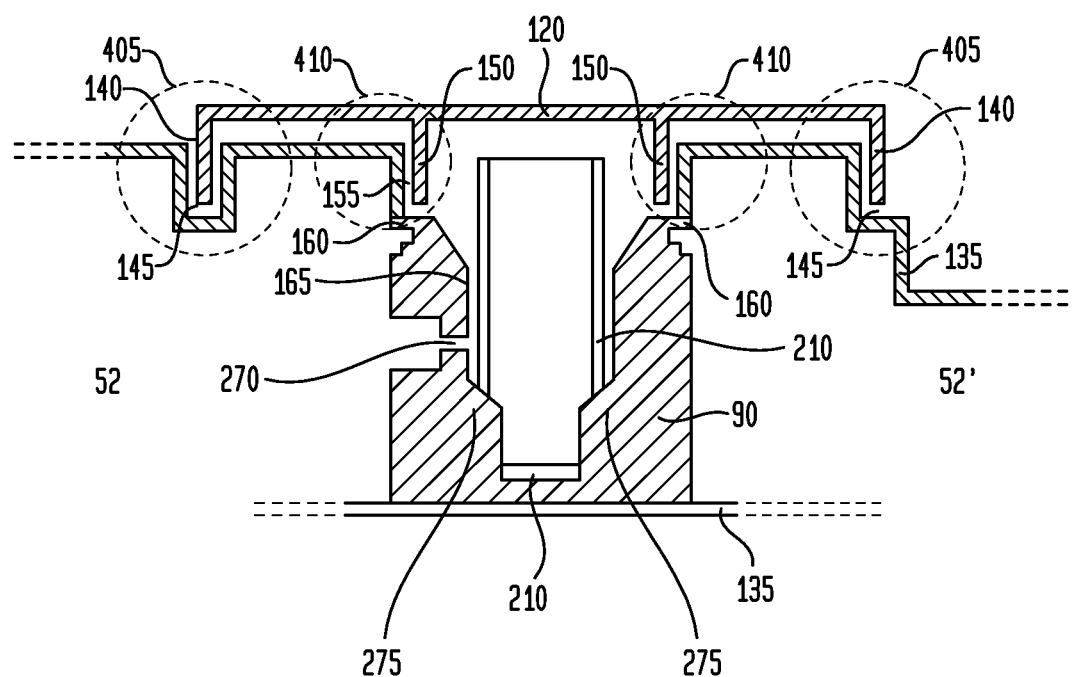

FIG. 23 is a cross-sectional view (through the 52-52' plane of FIG. 1) illustrating an exemplary sensor chamber cover 120, sensor chamber 90, cuvette 210, and a portion of the apparatus housing 135. Referring to FIGS. 1, 2, 9 and 23, numerous advantageous features of the exemplary embodiments are illustrated for minimizing or diminishing potential interference from extraneous light sources. First, the sensor chamber cover 120, sensor chamber 90, and apparatus housing 135 are configured to create two separate and independent light baffles 405 and 410. The sensor chamber cover 120 has a protruding or elongated rim 140, designed to mate with a recess or cavity 145 formed in the apparatus housing 135, to create a first, outer light baffle 405, illustrated in cross-section in FIG. 23. The sensor chamber cover 120 also has a protruding or elongated inner ring structure 150, designed to mate with a recess or cavity 155 formed in the apparatus housing 135, to create a second, inner light baffle 410, also illustrated in cross-section in FIG. 23.

Other additional features of the apparatus housing 135 are designed to diminish potential interference from extraneous light sources and also diminish potential damage from external fluids, as the apparatus 100 will typically be utilized in or near environments having water, such as rivers, drinking supplies, etc. First, not separately illustrated, all or most of the apparatus housing 135 and its various components (such as the sensor chamber 90 and the interior surfaces of the sensor chamber cover 120) comprise a flat black color, to minimize or diminish internal reflections. As the apparatus housing 135 is typically formed from a plastic or other polymer in top and bottom portions (e.g., a clamshell housing), which after assembly of the various components, are then coupled together to form the handheld device, a sealing O-ring 365 (typically comprising a plastic, rubber or other polymer material) is utilized at the junction of the top and bottom portions, as illustrated in FIG. 9 lining a portion of the interior of the housing 135. A seal 370 is also utilized over the outer or external part of the I/O interface 125, also to seal against light and fluids. In addition, magnetic closures 170 are utilized on the sensor chamber cover 120, having mating magnetic structures in the apparatus housing 135 (not separately illustrated), to maintain the sensor chamber cover 120 in a closed position during calibration and sample analysis.

Other features of the apparatus 100 may also be optionally included. For example, the apparatus may automatically assign a sample number and record a date and time for each sample. Such information may be stored in memory 310 or output via the I/O interface 125, for example.

Lastly, the ease of use of the apparatus 100 and system 300 cannot be underestimated, requiring very few steps (3-4) to complete a fluorimetric analysis, and is a significant advance over existing fluorimetric methods. First, a test sample is preconditioned by the user, as may be needed. Second, the system 300 is assembled by the user, namely, a cuvette 210 is inserted into the sensor chamber 90 of the apparatus 100, a sensor reagent housing 200 (having a reagent frit 190) is placed over the cuvette 210 and sensor chamber 90, a syringe 205 having a (pre-conditioned) sample to be tested or calibrated is inserted into the nozzle fitting 195, and the contents of the syringe are expelled through the sensor reagent housing 200 and into the cuvette 210. Third, the sensor reagent housing 200 and syringe 205 are removed, and the sensor chamber cover 120 is closed. Fourth, the user then presses a button, key or other input on the user interface 105, 105A, the analysis runs until completion under the control of the processor 305, with the analysis results displayed on the user interface 105, 105A (or output to another device or stored in memory 310). Calibration of the apparatus 100 is similarly easy, repeating the steps described above for each concentration of calibration samples.

Figure 24:
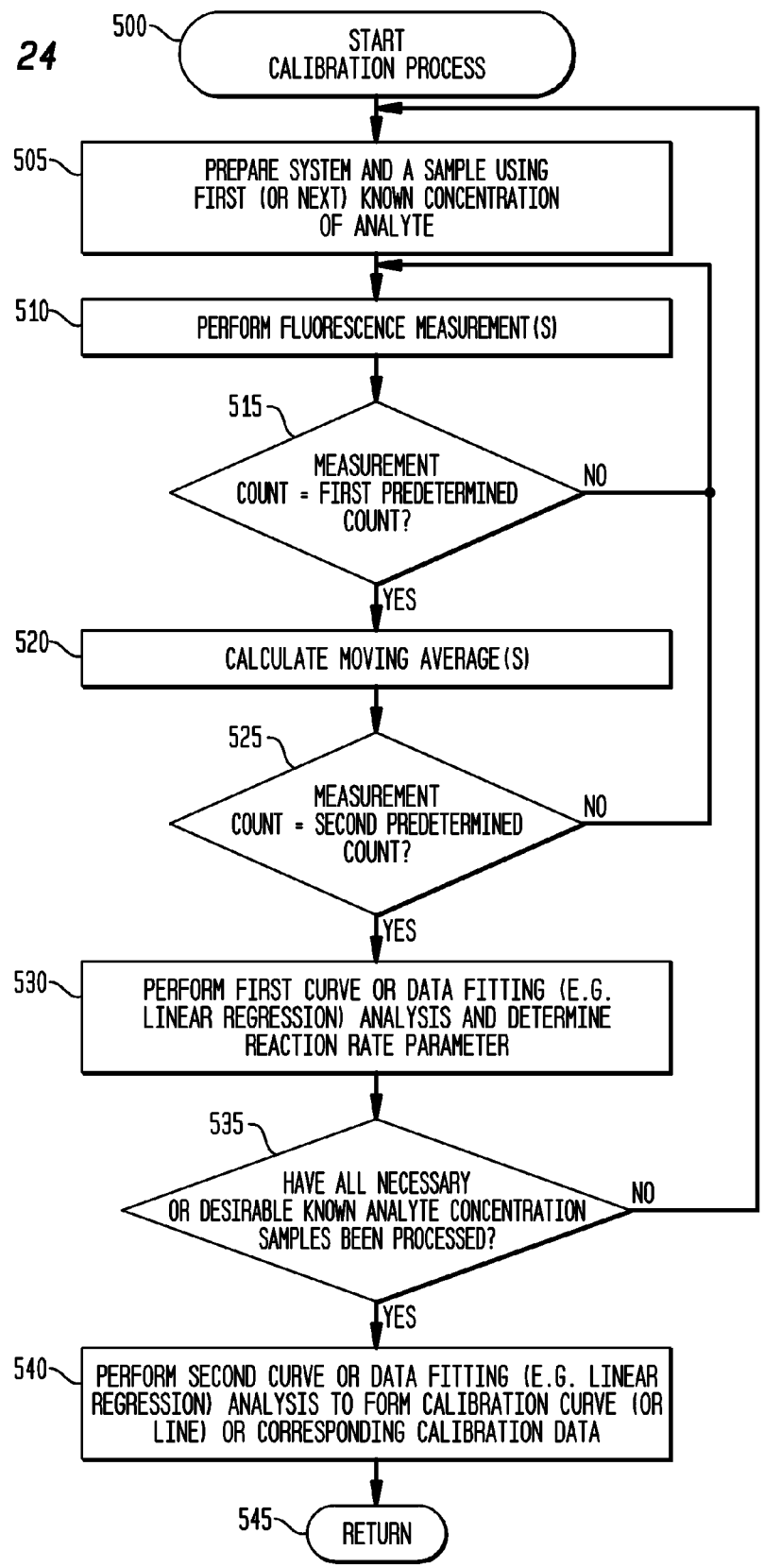

FIG. 24 is a flow chart illustrating an exemplary general (or standard) calibration method embodiment, and provides a useful summary. Beginning with start step 500, the user prepares the system 300 and a sample using a first (or next) known concentration of analyte, step 505, typically performing the second and third steps described above, of assembling the system for use and expelling the sample through the sensor reagent housing 200 into the cuvette 210, removing the sensor reagent housing 200 and syringe 205 and closing the sensor chamber cover 120. For calibration using a known concentration of analyte, typically provided as part of a kit, the calibration sample generally does not need preconditioning; otherwise, step 505 could include the first, preconditioning step described above. The apparatus 100 generally will also be placed or held on a horizontal, stable surface for sample analysis. Next, once initiated by the user through the user interface 105, 105A, the fluorescence measurements are performed, step 510, with this step and all remaining steps performed automatically by the apparatus 100. As fluorescence measurements are performed and digital fluorescence sample values (or data points) are generated, the processor 305 determines whether a measurement count has reached a first predetermined count, such as whether the first fifty digital fluorescence sample data values have been obtained, step 515, and if not, the method continues to perform fluorescence measurements and generate digital fluorescence sample data values, returning to step 510. When the first predetermined count has been reached in step 515, the processor 305 begins the determinations of the moving average data values, step 520. The processor 305 then determines whether a second predetermined measurement count has been reached, such as whether one hundred digital fluorescence sample data values or points have been generated, step 525, and if not, the method continues to perform fluorescence measurements and generate digital fluorescence sample data values, returning to step 510 and iterating. When the second predetermined count has been reached in step 525, indicating all of the digital fluorescence sample data points have been generated and moving average values calculated, the processor 305 performs a first curve or data fitting, such as a linear regression analysis, and determines the corresponding reaction rate parameter (such as a slope), step 530. The processor 305 then determines whether all of the necessary or desirable known analyte concentration samples have been processed, step 535, and if not, the method returns to step 505 to iterate for the next known concentration of analyte, prompting the user to prepare the system 300 and a calibration sample for the next calibration iteration for the next analyte concentration. If all of the calibration samples have been processed in step 535, the processor 305 performs a second curve or data fitting, such as a second linear regression analysis, to form a calibration curve or data fitting (or corresponding calibration data), step 540, for subsequent use in analysis of test samples, and the general calibration method may end, return step 545. It should be noted that once initiated by the user, following step 505, all remaining steps 510-545 are performed automatically by the apparatus 100.

Figure 25:
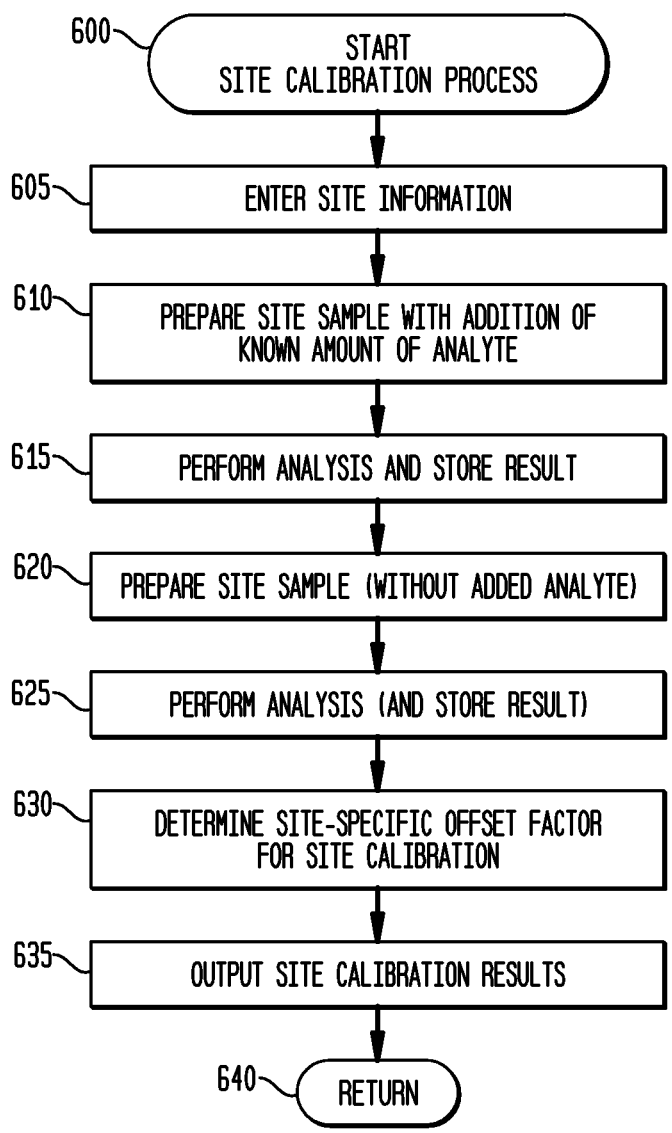

FIG. 25 is a flow chart illustrating an exemplary site calibration method embodiment, and provides a useful summary. Beginning with start step 600, the user enters site information into the apparatus 100, step 605, and prepares a site-specific sample with an addition of a known amount of the selected analyte (and which may also include the preconditioning discussed above), step 610. The user then initiates and the apparatus 100 performs the analyte concentration analysis discussed above (steps 510-530 discussed above or steps 710-730 discussed below), and the apparatus 100 stores the result, step 615. The user then prepares a site-specific sample (which may also include the preconditioning discussed above, but which does not include an addition of a known concentration of analyte), step 620. The user then initiates and the apparatus 100 performs the analysis discussed above (steps 510-530 discussed above or steps 710-730 discussed below), and the apparatus 100 optionally may also store the result, step 625. The apparatus 100 then determines a site-specific offset factor for site calibration, step 630, outputs the site calibration results (e.g., the screen image of FIG. 22), step 635, and the site calibration method may end, return step 640.

Figure 26:
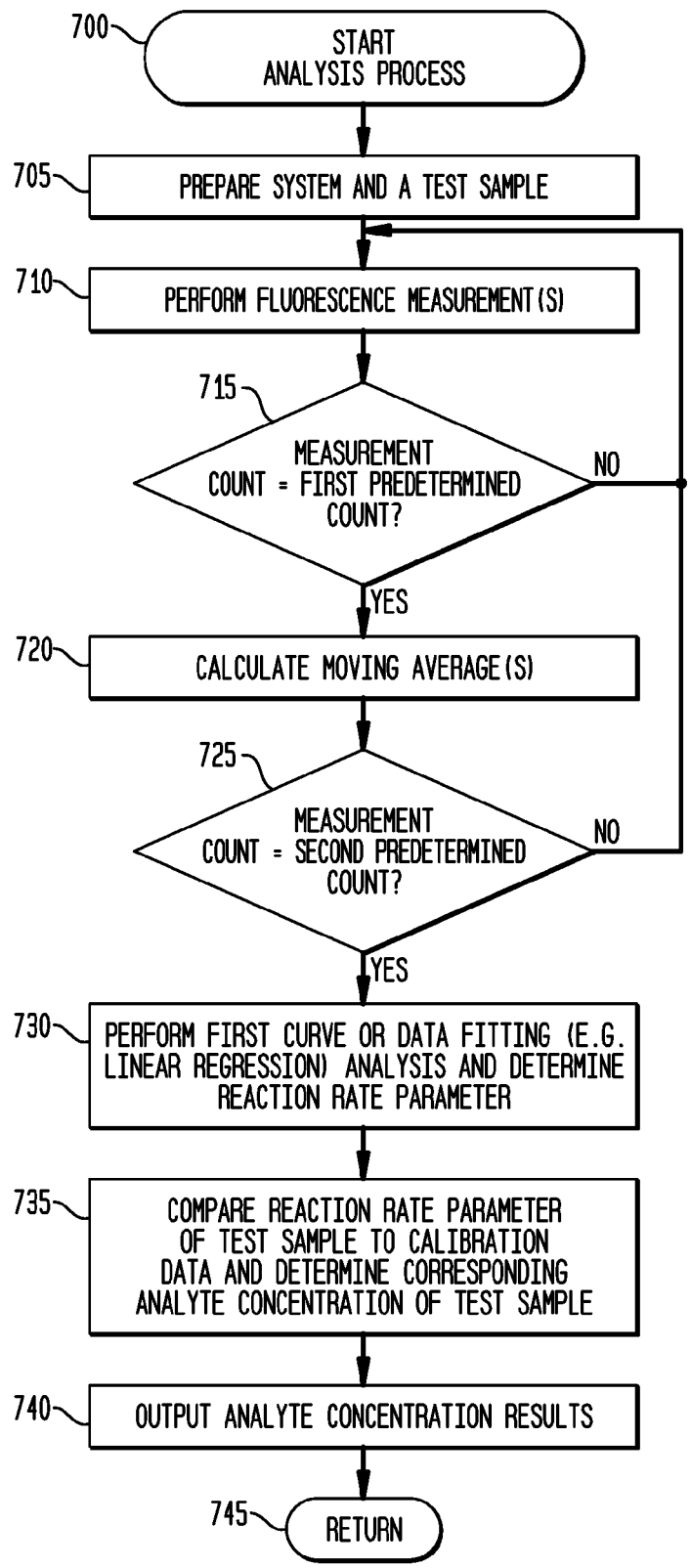

FIG. 26 is a flow chart illustrating an exemplary concentration detection method embodiment, and also provides a useful summary. Steps 700-730 are essentially the same as steps 500-530 of the calibration methodology, but performed with a test sample having an unknown analyte concentration, rather than with a calibration sample having a known analyte concentration. Beginning with start step 700, the user prepares the system 300 and a test sample, step 705, also typically performing the first, second and third steps described above, of preconditioning the sample (as may be necessary or desirable), of assembling the system for use, expelling the (preconditioned) test sample through the sensor reagent housing 200 and into the cuvette 210, removing the sensor reagent housing 200 and syringe 205 and closing the sensor chamber cover 120. The apparatus 100 generally will also be placed or held on a horizontal, stable surface for sample analysis. Next, once initiated by the user through the user interface 105, 105A, the fluorescence measurements are performed, step 710, with this step and all remaining steps performed automatically by the apparatus 100. As fluorescence measurements are performed and digital fluorescence sample data values or points are generated, the processor 305 determines whether a measurement count has reached a first predetermined count, such as whether the first fifty digital fluorescence sample data values or points have been obtained, step 715, and if not, the method continues to perform fluorescence measurements and generate digital fluorescence sample data values or points, returning to step 710. When the first predetermined count has been reached in step 715, the processor 305 begins the determinations of the moving average data values, step 720. The processor 305 then determines whether a second predetermined measurement count has been reached, such as whether one hundred digital fluorescence sample data values or points have been generated, step 725, and if not, the method continues to perform fluorescence measurements and generate digital fluorescence sample data values or points, returning to step 710 and iterating. When the second predetermined count has been reached in step 725, indicating all of the digital fluorescence sample data values or points have been generated and moving average values calculated, the processor 305 performs a curve or data fitting, such as a linear regression analysis, and determines the (corresponding) reaction rate parameter, step 730. The processor 305 then compares the reaction rate parameter of the test sample with the calibration data, and determines the corresponding analyte concentration of the test sample, step 735. The analyte concentration results are output, step 740, such as to the user interface 105, 105A and/or to the I/O interface 125, and the method may end, return step 745. It should be noted that once initiated by the user, following step 705, all remaining steps 710-745 are performed automatically by the apparatus 100. As determined by the user, the testing methodology may be repeated using additional test samples, as necessary or desirable, repeating steps 700-745.

Referring again to FIG. 9, the I/O interface 125 may be implemented as known or may become known in the art, to provide physical or wireless connection to a relevant channel, network or bus, to receive and transmit information of any kind or type, and may include corresponding driver circuitry, impedance matching capability, voltage translation for a low voltage processor to interface with a higher voltage control bus for example, various switching mechanisms (e.g., transistors) to turn various lines or connectors on or off in response to signaling from the processor 305, and/or physical coupling mechanisms. In addition, the I/O interface 125 may also be adapted to receive and/or transmit signals externally to the apparatus 100, such as through hard-wiring or RF signaling to a computer, a computer network, a communication network, an external memory, such as comprising one or more USB, RJ-11, RJ-45, Ethernet, Firewire, PCI bus, and/or ISA bus drivers, ports or connectors, or various wireless communication interfaces, such as cellular, Bluetooth, and GPS interfaces, for example, to receive information in real-time or to output results, and/or to provide geographic locations (such as of the test samples), also for example.

Also referring again to FIG. 9, a "processor" 305 may be any type of controller. processor or control logic circuit, and may be embodied as one or more processors 305, to perform the functionality discussed herein. As the term processor is used herein, a processor 305 may include use of a single integrated circuit ("IC"), or may include use of a plurality of integrated circuits or other components connected, arranged or grouped together, such as controllers, microprocessors, digital signal processors ("DSPs"), parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components. As a consequence, as used herein, the term processor should be understood to equivalently mean and include a single IC, or arrangement of custom ICs, ASICs, processors, microprocessors, controllers, FPGAs, adaptive computing ICs, or some other grouping of integrated circuits which perform the functions discussed below, with associated memory, such as microprocessor memory or additional RAM, DRAM, SDRAM, SRAM, MRAM, ROM, FLASH, EPROM or $E^2PROM$. A processor (such as processor 305), with its associated memory, may be adapted or configured (via programming, FPGA interconnection, or hard-wiring) to perform the methodology of the invention, such as calibration, curve or data fitting analysis, sample reaction rate parameter determination, etc. For example, the methodology may be programmed and stored, in a processor 305 with its associated memory (and/or memory 310) and other equivalent components, as a set of program instructions or other code (or equivalent configuration or other program) for subsequent execution when the processor is operative (i.e., powered on and functioning). Equivalently, when the processor 305 may implemented in whole or part as FPGAs, custom ICs and/or ASICs, the FPGAs, custom ICs or ASICs also may be designed, configured and/or hard-wired to implement the methodology of the invention. For example, the processor 305 may be implemented as an arrangement of processors, controllers, microprocessors, DSPs and/or ASICs, collectively referred to as a "controller" or "processor", which are respectively programmed, designed, adapted or configured to implement the methodology of the invention, in conjunction with a memory 310.

The memory 310, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a processor 305), whether volatile or non-volatile, whether removable or non-removable, including without limitation RAM, FLASH, DRAM, SDRAM, SRAM, MRAM, FeRAM, ROM, EPROM or $E^2PROM$, or any other form of memory device, such as a magnetic hard drive, an optical drive, a magnetic disk or tape drive, a hard disk drive, other machine-readable storage or memory media such as a floppy disk, a CDROM, a CD-RW, digital versatile disk (DVD) or other optical memory, or any other type of memory, storage medium, or data storage apparatus or circuit, which is known or which becomes known, depending upon the selected embodiment. In addition, such computer readable media includes any form of communication media which embodies computer readable instructions, data structures, program modules or other data in a data signal or modulated signal, such as an electromagnetic or optical carrier wave or other transport mechanism, including any information delivery media, which may encode data or other information in a signal, wired or wirelessly, including electromagnetic, optical, acoustic, RF or infrared signals, and so on. The memory 310 may be adapted to store various look up tables, parameters, coefficients, other information and data, programs or instructions (of the software of the present invention), and other types of tables such as database tables.

As indicated above, the processor 305 is programmed, using software and data structures of the invention, for example, to perform the methodology of the present invention. As a consequence, the method of the disclosure may be embodied as software which provides such programming or other instructions, such as a set of instructions and/or metadata embodied within a computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the disclosure may be embodied as any type of code, such as C, C++, SystemC, LISA, XML, Java, Brew, SQL and its variations, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the processor 305, for example).

The software, metadata, or other source code of the present invention and any resulting bit file (object code, database, or look up table) may be embodied within any tangible storage medium, such as any of the computer or other machine-readable data storage media, as computer-readable instructions, data structures, program modules or other data, such as discussed above with respect to the memory 310, e.g., a floppy disk, a CDROM, a CD-RW, a DVD, a magnetic hard drive, an optical drive, or any other type of data storage apparatus or medium, as mentioned above.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. One having skill in the art will further recognize that additional or equivalent method steps may be utilized, or may be combined with other steps, or may be performed in different orders, any and all of which are within the scope of the claimed invention. In addition, the various FIG.s are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment and not necessarily in all embodiments, and further, are not necessarily referring to the same embodiment. Furthermore, the particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the FIG.s can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

As used herein for purposes of the present invention, the term "LED" and its plural form "LEDs" should be understood to include any electroluminescent diode or other type of carrier injection- or junction-based system which is capable of generating radiation in response to an electrical signal, including without limitation, various semiconductor- or carbon-based structures which emit light in response to a current or voltage, light emitting polymers, organic LEDs, and so on, including within the visible spectrum, or other spectra such as ultraviolet or infrared, of any bandwidth, or of any color or color temperature.

The dimensions and values disclosed herein or in the related application are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Exemplary Embodiments are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Furthermore, any signal arrows in the drawings/FIG.s should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A portable fluorimetric system operative in field use to determine an analyte concentration of a plurality of samples, the system comprising in combination:
  a sensor reagent housing for injection of a sample for collection within a directional cuvette, the sensor reagent housing comprising:
  a porous substrate having an analysis chemistry reagent; and
  a sensor housing comprising a sensor cap and a sensor base, wherein the sensor cap comprises a first channel and a first interlocking region, the first channel having a first diameter at the first interlocking region; and wherein the sensor base comprises: a second interlocking region to mate with the first interlocking region; a second channel holding the porous substrate and in fluid communication with the first channel, the second channel having a second diameter greater than the first diameter; and a third channel coupled to and in fluid communication with the second channel, the third channel having a third diameter smaller than both the first diameter and the second diameter; and a fluorimetric apparatus comprising:
an apparatus housing;
a sensing chamber within the apparatus housing, the sensing chamber to removably hold the directional cuvette;
a sensing chamber cover movably coupled to the apparatus housing, the sensing chamber cover and apparatus housing together forming an inner light baffle and an outer light baffle over and around an upper portion of the sensing chamber;
a user interface arranged on an exterior of the apparatus housing, the user interface to display a plurality of user prompts including a start indicator for analysis initiation and a resulting analyte concentration in the sample;
a light source within an interior of the apparatus housing in optical communication with the sensing chamber to provide light to the sensing chamber;
a photomultiplier tube within the interior of the apparatus housing in optical communication with the sensing chamber to receive a fluorescence signal from the sensing chamber and generate a corresponding fluorescence voltage signal;
an amplifier within the interior of the apparatus housing and coupled to the photomultiplier tube to amplify the fluorescence voltage signal;
an analog-to-digital converter within the interior of the apparatus housing and coupled to the amplifier to generate a plurality of digital fluorescence sample data values in response to the amplified fluorescence voltage signal;
a memory within the interior of the apparatus housing, the memory adapted to store first calibration data for a first, apparatus calibration; a plurality of sets of second, site-specific calibration data, each set of second site-specific calibration data for a corresponding site of a plurality of sites; and a corresponding plurality of different site-specific offset factors, each site-specific offset factor specific for the corresponding site of the plurality of sites; and
a processor within the interior of the apparatus housing and coupled to the memory and to the analog-to-digital converter, the processor adapted to receive the digital fluorescence sample data values; to determine the first calibration data and the first, apparatus calibration; to determine the plurality of sets of second, site-specific calibration data and the corresponding plurality of different site-specific offset factors; to determine a first analyte concentration of a first sample from a first selected site using the digital fluorescence sample data values of the first sample and a first modified apparatus calibration determined using a first site-specific offset factor for the first selected site; and to determine a second analyte concentration of a second sample from a second, different selected site using the digital fluorescence sample data values of the second sample and a second modified apparatus calibration determined using a second, different site-specific offset factor for the second selected site.

2. The fluorimetric system of claim 1, wherein the sensor reagent housing further comprises:
interior housing walls to fit within an interior of the directional cuvette and direct liquid flow into the interior of the directional cuvette; and
exterior housing walls to fit over and around the exterior of the directional cuvette while seated on an upper, exterior surface of the sensing chamber.

3. The fluorimetric system of claim 2, wherein the analysis chemistry reagent is a nucleic acid analysis chemistry reagent.

4. The fluorimetric system of claim 2, wherein the sensor reagent housing further comprises a nozzle fitting couplable to a syringe for injection of the sample through the channel and porous medium for collection in the cuvette.

5. The fluorimetric system of claim 1, wherein during analyte concentration determination, the light source is adapted to provide continuous light to the sensing chamber and the photomultiplier tube further is to provide a continuous fluorescence voltage signal.

6. The fluorimetric system of claim 5, wherein during analyte concentration determination of each sample, the analog-to-digital converter further is adapted to generate a minimum of about fifty to one hundred digital fluorescence sample data values from the amplified, continuous fluorescence voltage signal to form the corresponding plurality of digital fluorescence sample data values for each sample.

7. The fluorimetric system of claim 6, wherein the processor further is adapted to perform a data fitting and determine a sample reaction rate parameter for each sample from the plurality of digital fluorescence sample data values corresponding to the sample.

8. The fluorimetric system of claim 7, wherein the data fitting is selected from the group consisting of: a linear regression and the sample reaction rate parameter corresponds to a slope of a line generated by the linear regression; exponential and the sample reaction rate parameter corresponds to an exponent; non-linear and the sample reaction rate parameter corresponds to a non-linear parameter; and combinations thereof.

9. The fluorimetric system of claim 7, wherein the processor further is adapted to determine the first analyte concentration from a comparison of a first sample reaction rate parameter for the first sample with the first modified apparatus calibration, the first modified apparatus calibration comprising the first, apparatus calibration data mathematically modified by the first site-specific offset factor, and wherein the processor further is adapted to determine the second analyte concentration from a comparison of a second sample reaction rate parameter for the second sample with the second modified apparatus calibration, the second modified apparatus calibration comprising the first, apparatus calibration data mathematically modified by the second site-specific offset factor.

10. The fluorimetric system of claim 7, wherein the processor further is adapted to determine the first analyte concentration from a comparison of a first sample reaction rate parameter for the first sample with the first modified apparatus calibration, the first modified apparatus calibration comprising the first, apparatus calibration data multiplied by the first site-specific offset factor, and wherein the processor further is adapted to determine the second analyte concentration from a comparison of a second sample reaction rate parameter for the second sample with the second modified apparatus calibration, the second modified apparatus calibration comprising the first, apparatus calibration data multiplied by the second site-specific offset factor.

11. The fluorimetric system of claim 7, wherein the processor further is adapted to determine the first analyte concentration from a comparison of a first sample reaction rate parameter for the first sample with the first modified apparatus calibration, the first modified apparatus calibration comprising the arithmetic sum of the first, apparatus calibration data plus the first site-specific offset factor, and wherein the processor further is adapted to determine the second analyte concentration from a comparison of a second sample reaction rate parameter for the second sample with the second modified apparatus calibration, the second modified apparatus calibration comprising the arithmetic sum of the first, apparatus calibration data plus the second site-specific offset factor.

12. The fluorimetric system of claim 7, wherein the processor further is adapted to determine a plurality of moving averages from the plurality of digital fluorescence sample data values, and to perform the data fitting using the plurality of moving averages to determine the sample reaction rate parameter.

13. The fluorimetric system of claim 7, wherein the processor further is adapted to use a first sample reaction rate parameter for the first sample and interpolate the first modified apparatus calibration to determine the first analyte concentration, the first modified apparatus calibration comprising the first, apparatus calibration data mathematically modified by the first site-specific offset factor.

14. The fluorimetric system of claim 7, wherein the processor further is adapted to compare a first sample reaction rate parameter for the first sample to linearized first modified apparatus calibration data, the first, apparatus calibration data generated from determining a plurality of reaction rates from a corresponding plurality of calibration samples having known analyte concentrations, the first modified apparatus calibration comprising the first, apparatus calibration data multiplied by the first site-specific offset factor.

15. The fluorimetric system of claim 1, wherein the processor further is adapted to determine the first, apparatus calibration data by performing a first data fitting and determining a first calibration sample reaction rate parameter or next calibration sample reaction rate parameter from the plurality of digital fluorescence sample data values corresponding to first or next known analyte concentration, generating a plurality of calibration sample reaction rate parameters corresponding to a plurality of different known analyte concentrations, and performing a second data fitting using the plurality of calibration sample reaction rate parameters to generate the first apparatus calibration.

16. The fluorimetric system of claim 15, wherein the processor further is adapted to determine the first site-specific offset factor as a first parameter for multiplication or addition with the first apparatus calibration data to provide the first modified apparatus calibration for the first selected site, and wherein the processor further is adapted to determine the different, second site-specific offset factor as a second parameter for multiplication or addition with the first apparatus calibration data to provide the second modified apparatus calibration for the first selected site.

17. The fluorimetric system of claim 1, wherein the processor further is adapted to determine the first site-specific offset factor by comparing data from a first calibration sample from the first selected site using the first, apparatus calibration, with data from a second calibration sample from the first selected site having an addition of a known amount of analyte and also using the first, apparatus calibration; and wherein the processor further is adapted to determine the second site-specific offset factor by comparing data from a first calibration sample from the second selected site using the first, apparatus calibration, with data from a second calibration sample from the second selected site having an addition of a known amount of analyte and also using the first, apparatus calibration.

18. The fluorimetric system of claim 1, wherein the user interface further comprises:
a visual display to display user prompts, site data, and analyte concentrations; and
a keypad for user response to user prompts displayed on the visual display.

19. The fluorimetric system of claim 1, wherein the system further comprises the directional cuvette, and wherein the cuvette has a plurality of substantially flat, rectangular sides.

20. The fluorimetric system of claim 19, wherein two opposing sides of the directional cuvette are recessed and two opposing sides of the directional cuvette are non-recessed, and wherein the sensing chamber further comprises at least one extension or flange which allows complete seating of the directional cuvette in the sensing chamber when the directional cuvette is in a first orientation and which blocks at least one of the non-recessed sides and prevents complete seating of the directional cuvette in the sensing chamber when the directional cuvette is in the second orientation.

21. The fluorimetric system of claim 1, wherein the light source comprises:
a light emitting diode to generate the light;
a first bandpass filter for wavelengths centered in a first band; and
a first lens to focus the light on an interior center of the cuvette.

22. The fluorimetric system of claim 21, further comprising:
a second lens to collect the fluorescence signal from the interior center of the cuvette, the second lens arranged substantially at a right angle to the first lens, the fluorescence signal emitted in wavelengths centered in a second band different than the first band; and
a second bandpass filter for wavelengths centered in a third band offset from the center of the second band.

23. The fluorimetric system of claim 22, wherein the first band is centered at about 485 nm, the second band is centered at about 518 nm, and the third band is centered between about 530 nm to about 535 nm.

24. The fluorimetric system of claim 1, further comprising:
an input/output interface disposed on the exterior of the apparatus housing and coupled to the processor, wherein the input/output interface comprises a USB driver and port or an Ethernet driver and port.

25. The fluorimetric system of claim 1, wherein the apparatus housing further comprises a plurality of interior, substantially optically non-reflective surfaces.

26. The fluorimetric system of claim 1, wherein the apparatus housing further comprises a polymer shell structure comprising two parts and a polymer or rubber sealing O-ring disposed about an interior of an interface between the two parts.

27. The fluorimetric system of claim 1, wherein the outer light baffle comprises:
an elongated rim of the sensing chamber cover; and
a mating recess in the apparatus housing.

28. The fluorimetric system of claim 1, wherein the inner light baffle comprises:
a protruding inner ring structure of the sensing chamber cover; and a mating recess in the apparatus housing.

29. The fluorimetric system of claim 1, wherein the apparatus housing has a size adapted to fit into a user's hand.

30. The fluorimetric system of claim 1, wherein the lowest detectable analyte concentration is in the parts per billion range.

31. A method of operating the system of claim 1 for analyte concentration determination by a user in two steps, the method comprising:
 in a first step, injecting the sample through the sensor reagent housing having a channel and a porous medium in the channel and moving the sensing chamber cover into a closed position, the porous medium having one or more nucleic acid analysis chemistry reagents, with the mixture of the sample and the one or more nucleic acid analysis chemistry reagents collecting in the directional cuvette; and
 in a second-step, responding to or actuating the start indicator to commence analyte concentration determination.

32. The method of operating the system of claim 31, further comprising:
 observing the analyte concentration result displayed on the user interface; and
 responding to a user prompt to save the analyte concentration result in the memory.

33. A method of calibrating the system of claim 31 by a user for the first apparatus calibration, the method comprising:
 performing the first and second steps using a plurality of known samples, each known sample having a different known analyte concentration.

34. A method of calibrating the system of claim 31 by a user for a first site specific calibration, the method comprising:
 performing the first and second steps using a sample from the first site; and
 performing the first and second steps using a sample from the first site having an addition of a known concentration or amount of analyte.

35. A fluorimetric system to determine an analyte concentration of a plurality of samples, the system comprising, in combination:
 a sensor reagent housing for injection of a sample for collection within a directional cuvette, the sensor reagent housing comprising:
  a porous substrate having an analysis chemistry reagent; and
  a sensor housing comprising a sensor cap and a sensor base, wherein the sensor cap comprises a first channel and a first interlocking region, the first channel having a first diameter at the first interlocking region; and wherein the sensor base comprises: a second interlocking region to mate with the first interlocking region; a second channel holding the porous substrate and in fluid communication with the first channel, the second channel having a second diameter greater than the first diameter; and a third channel coupled to and in fluid communication with the second channel, the third channel having a third diameter smaller than both the first diameter and the second diameter; and
 a fluorimetric apparatus comprising:
  an apparatus housing having a size adapted to fit into a user's hand;
  a sensing chamber within the apparatus housing, the sensing chamber to removably hold a directional cuvette;
  a sensing chamber cover movably coupled to the apparatus housing;
  a user interface arranged on an exterior of the apparatus housing, the user interface to display a plurality of user prompts including a start indicator for analysis initiation, the user interface further to display the analyte concentration in the sample following the analysis initiation;
  first optical circuitry to provide light to the sensing chamber and generate a corresponding fluorescence voltage signal;
  second circuitry to generate a plurality of digital fluorescence sample data values in response to the fluorescence voltage signal;
  a memory within the interior of the apparatus housing, the memory adapted to store first calibration data for a first, apparatus calibration; and a plurality of different site-specific offset factors, each site-specific offset factor specific for a corresponding site of a plurality of different sites; and
  a processor within the interior of the apparatus housing and coupled to the memory and to the second circuitry, the processor adapted to receive the digital fluorescence sample data values; to determine the first calibration data and the first, apparatus calibration; to determine the plurality of different site-specific offset factors; to determine a first analyte concentration of a first sample from a first site using the digital fluorescence sample data values of the first sample and a first modified apparatus calibration determined using a first site-specific offset factor for the first site; and to determine a second analyte concentration of a second sample from a second, different site using the digital fluorescence sample data values of the second sample and a second modified apparatus calibration determined using a second, different site-specific offset factor for the second site.

36. The fluorimetric apparatus of claim 35, wherein the first optical circuitry comprises a light source and a photomultiplier tube, and wherein during analyte concentration determination, the light source is adapted to provide continuous light to the sensing chamber and the photomultiplier tube further is to provide a continuous fluorescence voltage signal.

37. The fluorimetric apparatus of claim 36, wherein the light source comprises:
 a light emitting diode to generate the light;
 a first bandpass filter for wavelengths centered in a first band; and
 a first lens to focus the light on an interior center of the directional cuvette.

38. The fluorimetric apparatus of claim 37, wherein the first optical circuitry further comprises:
 a second lens to collect a fluorescence signal from the interior center of the cuvette, the second lens arranged substantially at a right angle to the first lens, the fluorescence signal emitted in wavelengths centered in a second band different than the first band; and
 a second bandpass filter for wavelengths centered in a third band offset from the center of the second band.

39. The fluorimetric apparatus of claim 38, wherein the first band is centered at about 485 nm, the second band is centered at about 518 nm, and the third band is centered between about 530 nm to about 535 nm.

40. The fluorimetric apparatus of claim 36, wherein the second circuitry comprises an amplifier and an analog-to-digital converter, and wherein during analyte concentration determination of each sample, the amplifier is to amplify the continuous fluorescence voltage signal and the analog-to-digital converter is to generate a minimum of about fifty to one hundred digital fluorescence sample data values from the amplified, continuous fluorescence voltage signal to form the corresponding plurality of digital fluorescence sample data values for each sample.

41. The fluorimetric apparatus of claim 35, wherein the processor further is adapted to perform a data fitting and determine a sample reaction rate parameter for each sample from the plurality of digital fluorescence sample data values corresponding to the sample.

42. The fluorimetric apparatus of claim 41, wherein the data fitting is selected from the group consisting of: a linear regression and the sample reaction rate parameter corresponds to a slope of a line generated by the linear regression; exponential and the sample reaction rate parameter corresponds to an exponent; non-linear and the sample reaction rate parameter corresponds to a non-linear parameter; and combinations thereof.

43. The fluorimetric apparatus of claim 41, wherein the processor further is adapted to determine the first analyte concentration from a comparison of a first sample reaction rate parameter for the first sample with the first modified apparatus calibration, the first modified apparatus calibration comprising the first, apparatus calibration data mathematically modified by the first site-specific offset factor, and wherein the processor further is adapted to determine the second analyte concentration from a comparison of a second sample reaction rate parameter for the second sample with the second modified apparatus calibration, the second modified apparatus calibration comprising the first, apparatus calibration data mathematically modified by the second site-specific offset factor.

44. The fluorimetric apparatus of claim 41, wherein the processor further is adapted to determine the first analyte concentration from a comparison of a first sample reaction rate parameter for the first sample with the first modified apparatus calibration, the first modified apparatus calibration comprising the first, apparatus calibration data multiplied by the first site-specific offset factor, and wherein the processor further is adapted to determine the second analyte concentration from a comparison of a second sample reaction rate parameter for the second sample with the second modified apparatus calibration, the second modified apparatus calibration comprising the first, apparatus calibration data multiplied by the second site-specific offset factor.

45. The fluorimetric apparatus of claim 41, wherein the processor further is adapted to determine the first analyte concentration from a comparison of a first sample reaction rate parameter for the first sample with the first modified apparatus calibration, the first modified apparatus calibration comprising the arithmetic sum of the first, apparatus calibration data plus the first site-specific offset factor, and wherein the processor further is adapted to determine the second analyte concentration from a comparison of a second sample reaction rate parameter for the second sample with the second modified apparatus calibration, the second modified apparatus calibration comprising the arithmetic sum of the first, apparatus calibration data plus the second site-specific offset factor.

46. The fluorimetric apparatus of claim 41, wherein the processor further is adapted to determine a plurality of moving averages from the plurality of digital fluorescence sample data values, and to perform the data fitting using the plurality of moving averages to determine the sample reaction rate parameter.

47. The fluorimetric apparatus of claim 41, wherein the processor further is adapted to use a first sample reaction rate parameter for the first sample and interpolate the first modified apparatus calibration to determine the first analyte concentration, the first modified apparatus calibration comprising the first, apparatus calibration data mathematically modified by the first site-specific offset factor.

48. The fluorimetric apparatus of claim 41, wherein the processor further is adapted to compare a first sample reaction rate parameter for the first sample to linearized first modified apparatus calibration data, the first, apparatus calibration data generated from determining a plurality of reaction rates from a corresponding plurality of calibration samples having known analyte concentrations, the first modified apparatus calibration comprising the first, apparatus calibration data multiplied by the first site-specific offset factor.

49. The fluorimetric apparatus of claim 35, wherein the processor further is adapted to determine the first, apparatus calibration data by performing a first data fitting and determining a first calibration sample reaction rate parameter or next calibration sample reaction rate parameter from the plurality of digital fluorescence sample data values corresponding to first or next known analyte concentration, generating a plurality of calibration sample reaction rate parameters corresponding to a plurality of different known analyte concentrations, and performing a second data fitting using the plurality of calibration sample reaction rate parameters to generate the first apparatus calibration.

50. The fluorimetric apparatus of claim 49, wherein the processor further is adapted to determine the first site-specific offset factor as a first parameter for multiplication or addition with the first apparatus calibration data to provide the first modified apparatus calibration for the first selected site, and wherein the processor further is to determine the different, second site-specific offset factor as a second parameter for multiplication or addition with the first apparatus calibration data to provide the second modified apparatus calibration for the first selected site.

51. The fluorimetric apparatus of claim 35, wherein the processor further is adapted to determine the first site-specific offset factor by comparing data from a first calibration sample from the first selected site using the first, apparatus calibration, with data from a second calibration sample from the first selected site having an addition of a known amount of analyte and also using the first, apparatus calibration; and wherein the processor further is adapted to determine the second site-specific offset factor by comparing data from a first calibration sample from the second selected site using the first, apparatus calibration, with data from a second calibration sample from the second selected site having an addition of a known amount of analyte and also using the first, apparatus calibration.

52. The fluorimetric apparatus of claim 35, wherein the user interface further comprises:
 a visual display to display user prompts, site data, and analyte concentrations; and
 a keypad for user response to user prompts displayed on the visual display.

53. The apparatus of claim 35, wherein the apparatus is portable and operative in field use.

54. A method of operating the apparatus of claim 35 for analyte concentration determination by a user in two steps, the method comprising:
 in a first step, injecting the sample through a sensor reagent housing having a channel and a porous medium in the channel and moving the sensing chamber cover into a closed position, the porous medium having one or more nucleic acid analysis chemistry reagents, with the mixture of the sample and the one or more nucleic acid analysis chemistry reagents collecting in a directional cuvette in the sensing chamber; and in a second-step, responding to or actuating the start indicator to commence analyte concentration determination.

55. The method of operating the apparatus of claim 54, further comprising:

observing the analyte concentration result displayed on the user interface; and responding to a user prompt to save the analyte concentration result in the memory.

56. A method of calibrating the apparatus of claim 54 by a user for the first apparatus calibration, the method comprising:

performing the first and second steps using a plurality of known samples, each known sample having a different known analyte concentration.

57. A method of calibrating the apparatus of claim 54 by a user for a first site specific calibration, the method comprising:

performing the first and second steps using a sample from the first site; and performing the first and second steps using a sample from the first site having an addition of a known concentration or amount of analyte.

58. A portable fluorimetric system operative in field use to determine an analyte concentration of a plurality of samples in a user interactive, two-step process per sample, the system comprising:

a single-use sensor reagent housing having a nucleic acid analysis chemistry reagent, through which a sample is injected for collection within a directional cuvette in a first step of the two-step process, the single-use sensor reagent housing comprising:

a porous substrate having the nucleic acid analysis chemistry reagent; and a sensor housing comprising a sensor cap and a sensor base, wherein the sensor cap comprises a first channel and a first interlocking region, the first channel having a first diameter at the first interlocking region; and wherein the sensor base comprises: a second interlocking region to mate with the first interlocking region;

wherein the sensor housing further comprises a second channel at the coupling of the sensor cap and sensor base, the second channel holding the porous substrate and in fluid communication with the first channel, the second channel having a second diameter greater than the first diameter; and the sensor base further comprising a third channel coupled to and in fluid communication with the second channel, the third channel having a third diameter smaller than both the first diameter and the second diameter; and a fluorimetric apparatus comprising:

an apparatus housing having a size adapted to fit into a user's hand;

a sensing chamber within the apparatus housing, the sensing chamber to removably hold the directional cuvette;

a sensing chamber cover movably coupled to the apparatus housing, the sensing chamber cover and apparatus housing together forming an inner light baffle and an outer light baffle over and around an upper portion of the sensing chamber;

a user interface arranged on an exterior of the apparatus housing, the user interface to display a plurality of user prompts including a start indicator for analysis initiation in the second step of the two-step process, the user interface further to display the analyte concentration in the sample following the analysis initiation;

first optical circuitry to provide light to the sensing chamber and generate a corresponding fluorescence voltage signal;

second circuitry to generate a plurality of digital fluorescence sample data values in response to the fluorescence voltage signal;

a memory within the interior of the apparatus housing, the memory adapted to store a first, apparatus calibration and a plurality of different site-specific offset factors, each site-specific offset factor specific for a corresponding site of a plurality of different sites; and a processor within the interior of the apparatus housing and coupled to the memory and to the second circuitry, the processor adapted to receive the digital fluorescence sample data values; to determine the first, apparatus calibration; to determine the plurality of different site-specific offset factors using the first apparatus calibration; to determine a first analyte concentration of a first sample from a first site using the digital fluorescence sample data values of the first sample and a first modified apparatus calibration determined using a first site-specific offset factor for the first site; and to determine a second analyte concentration of a second sample from a second, different site using the digital fluorescence sample data values of the second sample and a second modified apparatus calibration determined using a second, different site-specific offset factor for the second site.

59. The fluorimetric system of claim 58, wherein the first optical circuitry comprises:

a light emitting diode in optical communication with the sensing chamber to provide continuous light to the sensing chamber during analyte concentration determination;

a first bandpass filter for wavelengths in a first band centered at about 485 nm; and a first lens to focus the light on an interior center of the directional cuvette;

a second lens to collect a fluorescence signal from the interior center of the cuvette, the second lens arranged substantially at a right angle to the first lens, the fluorescence signal emitted in wavelengths in a second band centered at about 518 nm;

a second bandpass filter for wavelengths centered in a third band centered between about 530 nm to about 535 nm; and a photomultiplier tube in optical communication with the sensing chamber to receive a fluorescence signal from the sensing chamber and to provide a continuous fluorescence voltage signal.

60. The fluorimetric system of claim 58, wherein the second circuitry comprises an amplifier and an analog-to-digital converter, and wherein during analyte concentration determination of each sample, the amplifier is to amplify the continuous fluorescence voltage signal and the analog-to-digital converter is to generate a minimum of about fifty to one hundred digital fluorescence sample data values from the amplified, continuous fluorescence voltage signal to form the corresponding plurality of digital fluorescence sample data values for each sample.

61. The fluorimetric system of claim 58, wherein the processor further is adapted to determine the first analyte concentration from a comparison of a first sample reaction rate parameter for the first sample with the first modified apparatus calibration, the first modified apparatus calibration comprising the first, apparatus calibration data multiplied by the first site-specific offset factor, and wherein the processor further is adapted to determine the second analyte concentration from a comparison of a second sample reaction rate parameter for the second sample with the second modified apparatus calibration, the second modified apparatus calibration comprising the first, apparatus calibration data multiplied by the second site-specific offset factor.

62. The fluorimetric system of claim 58, wherein the processor further is adapted to determine the first site-specific offset factor by comparing data from a first calibration sample from the first selected site using the first, apparatus calibration, with data from a second calibration sample from the first selected site having an addition of a known amount of analyte and also using the first, apparatus calibration; and wherein the processor further is adapted to determine the second site-specific offset factor by comparing data from a first calibration sample from the second selected site using the first, apparatus calibration, with data from a second calibration sample from the second selected site having an addition of a known amount of analyte and also using the first, apparatus calibration.

63. A method of operating the system of claim 58 for analyte concentration determination by a user in two steps, the method comprising:
   in a first step, injecting the sample through the sensor reagent housing and moving the sensing chamber cover into a closed position, with the mixture of the sample and the one or more nucleic acid analysis chemistry reagents collecting in the directional cuvette in the sensing chamber; and
   in a second-step, responding to or actuating the start indicator to commence analyte concentration determination.

64. A method of calibrating the system of claim 63 by a user for the first apparatus calibration, the method comprising:
   performing the first and second steps using a plurality of known samples, each known sample having a different known analyte concentration.

65. A method of calibrating the system of claim 63 by a user for a first site specific calibration, the method comprising:
   performing the first and second steps using a sample from the first site; and
   performing the first and second steps using a sample from the first site having an addition of a known concentration or amount of analyte.

66. A fluorimetric system for analyte concentration determination in a user interactive, two-step process per sample, the system comprising, in combination:
   a sensor reagent housing for injection of a sample for collection within a directional cuvette, the sensor reagent housing comprising:
   a porous substrate having one or more nucleic acid analysis chemistry reagents; and
   a sensor housing comprising a sensor cap and a sensor base, wherein the sensor cap comprises a first channel and a first interlocking region, the first channel having a first diameter at the first interlocking region; and
   wherein the sensor base comprises: a second interlocking region to mate with the first interlocking region;
   wherein the sensor housing further comprises a second channel at the coupling of the sensor cap and sensor base, the second channel holding the porous substrate and in fluid communication with the first channel, the second channel having a second diameter greater than the first diameter; and
   the sensor base further comprising a third channel coupled to and in fluid communication with the second channel, the third channel having a third diameter smaller than both the first diameter and the second diameter; and
a fluorimetric apparatus comprising:
   an apparatus housing;
   a sensing chamber within the apparatus housing, the sensing chamber to removably hold a directional cuvette to contain a mixture of the sample and one or more nucleic acid analysis chemistry reagents deposited by a user in a first step of the two-step process;
   a sensing chamber cover movably coupled to the apparatus housing, the sensing chamber cover and apparatus housing together forming an inner light baffle and an outer light baffle over and around an upper portion of the sensing chamber;
   a user interface arranged on an exterior of the apparatus housing, the user interface to display a plurality of user prompts including a start indicator for analysis initiation in a second step of the two-step process, the user interface further to display the analyte concentration in the sample following the analysis initiation;
   first optical circuitry to provide light to the sensing chamber and generate a corresponding fluorescence voltage signal;
   second circuitry to generate a plurality of digital fluorescence sample data values in response to the fluorescence voltage signal;
   a memory within the interior of the apparatus housing, the memory adapted to store a first, apparatus calibration and a plurality of different site-specific offset factors, each site-specific offset factor specific for a corresponding site of a plurality of different sites; and
   a processor within the interior of the apparatus housing and coupled to the memory and to the second circuitry, the processor adapted to receive the digital fluorescence sample data values; to determine a plurality of moving averages of the plurality of digital fluorescence sample data values; to determine the first, apparatus calibration by performing a first linear regression and determining a first calibration sample reaction rate parameter or next calibration sample reaction rate parameter from the plurality of moving averages of the plurality of digital fluorescence sample data values corresponding to first or next known analyte concentration, generating a plurality of calibration sample reaction rate parameters corresponding to a plurality of different known analyte concentrations, and performing a second linear regression using the plurality of calibration sample reaction rate parameters to generate the first apparatus calibration; to determine the plurality of different site-specific offset factors; to determine a first analyte concentration of a first sample from a first site using the digital fluorescence sample data values of the first sample and a first modified apparatus calibration determined using a first site-specific offset factor for the first site; and to determine a second analyte concentration of a second sample from a second, different site using the digital fluorescence sample data values of the second sample and a second modified apparatus calibration determined using a second, different site-specific offset factor for the second site.

* * * * *